United States Patent
Saito et al.

(10) Patent No.: US 6,653,342 B2
(45) Date of Patent: Nov. 25, 2003

(54) 13-SUBSTITUTED MILBEMYCIN DERIVATIVES, THEIR PREPARATION AND THEIR USE AGAINST INSECTS AND OTHER PESTS

(75) Inventors: Akio Saito, Chiba (JP); Yoko Sugiyama, Kawaguchi (JP); Toshimitsu Toyama, Kashiwa (JP); Toshihiko Nanba, Kawagoe (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/277,993

(22) Filed: Oct. 22, 2002

(65) Prior Publication Data

US 2003/0139601 A1 Jul. 24, 2003

Related U.S. Application Data

(63) Continuation-in-part of application No. PCT/JP01/03656, filed on Apr. 26, 2001.

(30) Foreign Application Priority Data

Apr. 27, 2000 (JP) .......................................... 2000-127209

(51) Int. Cl.[7] .............................................. A61K 31/335
(52) U.S. Cl. ........................ 514/450; 549/292; 504/292
(58) Field of Search ........................ 514/450; 504/292; 549/292

(56) References Cited

U.S. PATENT DOCUMENTS

| | | | |
|---|---|---|---|
| 4,171,314 A | 10/1979 | Chabala et al. | |
| 4,173,571 A | 11/1979 | Chabala et al. | |
| 4,201,861 A | 5/1980 | Mrozik et al. | |
| 4,203,976 A | 5/1980 | Fisher et al. | |
| 4,206,205 A | 6/1980 | Mrozik et al. | |
| 4,289,760 A | 9/1981 | Mrozik et al. | |
| 4,423,209 A | 12/1983 | Mrozik | |
| 4,457,920 A | 7/1984 | Mrozik | |
| 4,461,058 A | 7/1984 | Gaudino | |
| 4,547,491 A | 10/1985 | Mrozik et al. | |
| 4,547,520 A | 10/1985 | Ide et al. | |
| 4,579,864 A | 4/1986 | Linn et al. | |
| 4,963,582 A | 10/1990 | Sato et al. | |
| 5,405,867 A | 4/1995 | Sato et al. | |

FOREIGN PATENT DOCUMENTS

| | | |
|---|---|---|
| EP | 0 001 688 A | 5/1979 |
| EP | 0 008 184 A | 2/1980 |
| EP | 0 067 133 A | 12/1982 |
| EP | 0 102 721 A | 3/1984 |
| EP | 0 115 930 A | 8/1984 |
| EP | 0 180 539 A | 5/1986 |
| EP | 0 184 989 A | 6/1986 |
| EP | 0 203 832 B1 | 12/1986 |
| EP | 0 246 739 A | 11/1987 |
| EP | 0 342 710 A | 11/1989 |
| EP | 0 675 133 A | 10/1995 |
| EP | 0 765 879 A | 4/1997 |
| JP | 57-120589 A | 7/1982 |
| JP | 59-16894 A | 1/1984 |

*Primary Examiner*—Amelia Owens
(74) *Attorney, Agent, or Firm*—Frishauf, Holtz, Goodman & Chick, P.C.

(57) ABSTRACT

Compounds of formula (I) and salts thereof:

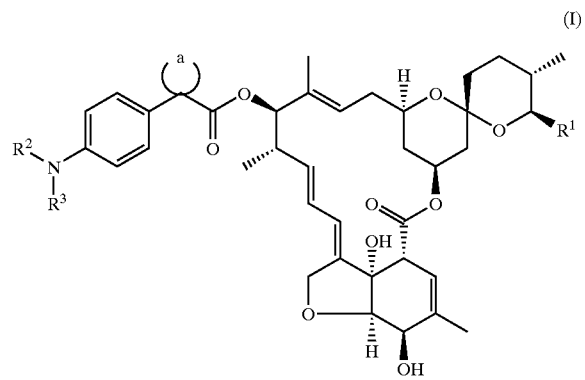

Wherein $R^1$ represents methyl, ethyl, isopropyl or s-butyl; and $R^2$ represents hydrogen or alkyl. $R^3$ represents hydrogen, optionally substituted alkanoyl, optionally substituted alkenoyl, optionally substituted alkynoyl, alkylsulfonyl, or alkoxycarbonyl, or $R^2$ and $R^3$ together with the nitrogen atom to which they are attached form a saturated, optionally substituted 4- to 6-membered heterocyclic ring group. The moiety -a- together with the carbon atom to which it is attached forms a 3- to 6-membered cycloalkyl group. These compounds have anthelmintic, acaricidal and insecticidal activity.

38 Claims, No Drawings

13-SUBSTITUTED MILBEMYCIN DERIVATIVES, THEIR PREPARATION AND THEIR USE AGAINST INSECTS AND OTHER PESTS

This application is a continuation-in-part of International Application PCT/JP01/03656 filed Apr. 26, 2001 which is hereby incorporated herein.

BACKGROUND OF THE INVENTION

The present invention relates to a series of new 13-substituted milbemycin derivatives which have valuable acaricidal, insecticidal and anthelmintic activities making them highly useful for protecting plants and animals, which may be human or non-human, from damage by parasites. The invention also provides methods and compositions for using these compounds as well as processes for their preparation.

There are several classes of known compounds with a structure based on a 16-membered macrolide ring, which are obtained by fermentation of various microorganisms or semi-synthetically by chemical derivatization of such natural fermentation products, and which exhibit acaricidal, insecticidal, anthelmintic and antiparasitic activities. The milbemycins and avermectins are examples of two such classes of known compounds, but others exist and are normally identified in the prior art by different names or code numbers. The names for these various macrolide compounds have generally been taken from the names or code numbers of the microorganisms which produce the naturally occurring members of each class, and these names have then been extended to cover the chemical derivatives of the same class, with the result that there has been no standardized systematic nomenclature for such compounds generally.

In order to avoid confusion, a standardized system of nomenclature will be used herein, which follows the normal rules for naming derivatives of organic compounds as recommended by the International Union of Pure and Applied Chemistry (IUPAC), Organic Chemistry Division, Commission on Nomenclature of Organic Chemistry, and which is based on the hypothetical parent compound hereby defined as "milbemycin", which is that compound represented by the following formula (A):

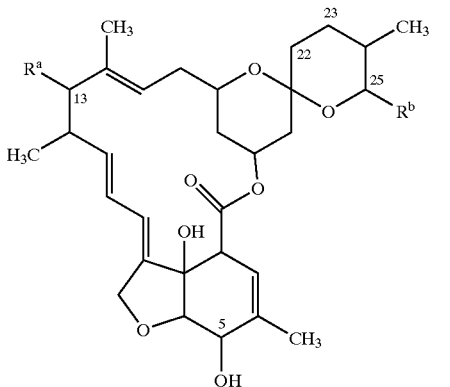

(A)

wherein $R^a$ and $R^b$ both represent hydrogen atoms.

For the avoidance of doubt, the above formula (A) also shows the numbering of positions of the macrolide ring system applied to those positions of most relevance to the compounds of the present invention.

The naturally produced milbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. No. 3,950,360. These compounds may be represented by the above formula (A) in which $R^a$ at position 13 is a hydrogen atom and $R^b$ at position 25 is a methyl group, an ethyl group or an isopropyl group, these compounds being designated as milbemycin $A_3$, milbemycin $A_4$ and milbemycin D, respectively. The milbemycin analog having a hydrogen atom at position 13 and substituted at position 25 with a sec-butyl group was disclosed in U.S. Pat. No. 4,173,571, where it was known as "13-deoxy-22,23-dihydroavermectin $B_{1a}$ aglycone".

Subsequently, various derivatives of the original milbemycins and avermectins have been prepared and their activities investigated. For example, 5-esterified milbemycins have been disclosed in U.S. Pat. Nos. 4,201,861, 4,206,205, 4,173,571, 4,171,314, 4,203,976, 4,289,760, 4,457,920, 4,579,864 and 4,547,491, in European Patent Publications No. 0008184, No. 0102721, No. 0115930, No. 0180539 and No. 0184989 and in Japanese Patent Applications Kokai (i.e. as laid open to public inspection) No. 57-120589 and 59-16894.

13-Hydroxy-5-ketomilbemycin derivatives have been disclosed in U.S. Pat. No. 4,423,209. Milbemycin 5-oxime derivatives were disclosed in U.S. Pat. No. 4,547,520 and in European Patent Publication No. 0203832.

Milbemycins having an ester bond at the 13-position are of particular relevance to the present invention and a number of compounds in which the 13-hydroxy group in the compounds of the above formula (A) has been esterified is disclosed in European Patent Publication No. 0186043, which describes esters of a variety of carboxylic acids such as the alkanoic acids. Other milbemycin derivatives having an ester bond at the 13-position, which probably represent the closest prior art, are described in European Patent Publications No. 0246739, No. 0675133 and No. 0765879. These, however, differ from the compounds of the present invention in the nature of the group at the 13-position and, in the case of European Patent Publication No. 0765879, the nature of the group at the 5-position.

The various classes of milbemycin-related macrolide compounds referred to above are all disclosed as having one or more types of activity as antibiotic, anthelmintic, ectoparasiticidal, acaricidal or other pesticidal agents. However, there is still a continuing need to provide such agents with improved activity against one or more classes of agricultural and horticultural pests.

It has now been discovered that the activity of such milbemycin-related derivatives can be improved by appropriately selecting the combination of substituents on the macrolide ring system, especially the substituents at position 13. In particular, it has now been found that the activity of the compounds can be improved upon by appropriate selection of certain highly specific ester groups at the 13 position, as specified below. The compounds of the present invention have been found to have a better pesticidal activity than do the compounds of the prior art, and many of the compounds of the present invention have a very substantially better activity.

BRIEF SUMMARY OF INVENTION

Accordingly, it is an object of the present invention to provide such milbemycin derivatives which have improved activity.

It is another object of the invention to provide methods for preparing such compounds.

It is a still further object of the invention to provide acaricidal, insecticidal and anthelmintic compositions and methods using the said compounds.

Other objects and advantages will become apparent as the description proceeds.

The present invention thus provides compounds of formula (I) and agriculturally, horticulturally, pharmaceutically and veterinarily acceptable salts thereof:

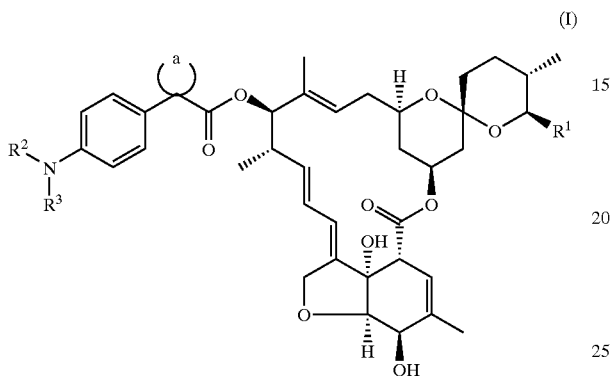

wherein:
- $R^1$ represents a methyl group, ethyl group, isopropyl group or s-butyl group;
- $R^2$ represents a hydrogen atom or an alkyl group having from 1 to 6 carbon atoms;
- $R^3$ represents a hydrogen atom, an alkanoyl group having from 1 to 6 carbon atoms which may optionally be substituted with 1, 2 or 3 substitutents selected independently from Substituents A defined below, an alkenoyl group having from 3 to 5 carbon atoms which may optionally be substituted with 1 or 2 substitutents selected independently from Substituents A defined below, an alkynoyl group having from 3 to 5 carbon atoms which may optionally be substituted with 1 or 2 substitutents selected independently from Substituents A defined below, an alkylsulfonyl group in which the alkyl moiety has from 1 to 6 carbon, or an alkoxycarbonyl group in which the alkoxy moiety has from 1 to 6 carbon atoms, or
- $R^2$ and $R^3$ together with the nitrogen atom to which they are attached form a saturated 4- to 6-membered heterocyclic ring group containing one ring nitrogen atom and optionally containing one further ring heteroatom selected from the group consisting of sulfur atoms, oxygen atoms and nitrogen atoms, said saturated heterocyclic ring optionally being substituted with 1 or 2 substituents independently selected from Substituents B defined below;
- the moiety -a- together with the carbon atom to which it is attached forms a 3- to 6-membered cycloalkyl group;
- Substituents A are selected from the group consisting of halogen atoms, cyano groups, hydroxy groups, alkoxy groups having from 1 to 6 carbon atoms, alkylthio groups having from 1 to 6 carbon atoms, alkanoyloxy groups having from 1 to 6 carbon atoms, amino groups which may optionally be substituted with 1 or 2 substituents selected from the group consisting of alkyl groups having from 1 to 6 carbon atoms, alkanoyl groups having from 1 to 6 carbon atoms, alkylsulfonyl groups in which the alkyl moiety has from 1 to 6 carbon and alkoxycarbonyl groups in which the alkoxy moiety has from 1 to 6 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with 1 or 2 substituents independently selected from Substituents B defined below;
- Substituents B are selected from the group consisting of halogen atoms, cyano groups, hydroxy groups, alkoxy groups having from 1 to 6 carbon atoms, alkylthio groups having from 1 to 6 carbon atoms, alkanoyloxy groups having from 1 to 6 carbon atoms, amino groups which may optionally be substituted with 1 or 2 substituents selected from the group consisting of alkyl groups having from 1 to 6 carbon atoms, alkanoyl groups having from 1 to 6 carbon atoms, alkylsulfonyl groups in which the alkyl moiety has from 1 to 6 carbon and alkoxycarbonyl groups in which the alkoxy moiety has from 1 to 6 carbon atoms and oxo groups.

The invention still further provides an anthelmintic, acaricidal and insecticidal composition comprising an anthelmintic, acaricidal and insecticidal compound in admixture with an agriculturally, horticulturally, pharmaceutically or veterinarily acceptable carrier or diluent, wherein said compound is selected from the group consisting of compounds of formula (I) and agriculturally, horticulturally, pharmaceutically or veterinarily acceptable salts thereof.

The invention still further provides a method of protecting plants and animals, which may be human or non-human, from damage by parasites selected from the group consisting of acarids, helminths and insects, which comprises applying an active compound to said plants or animals or to parts of or reproductive matter (e.g. seeds) of said plants or to a locus including said plants, said animals or parts of said plants or reproductive matter of said plants, wherein the active compound is selected from the group consisting of compounds of formula (I) and agriculturally, horticulturally, pharmaceutically or veterinarily acceptable salts thereof.

The invention still further provides the use of a compound of formula (I) or a pharmaceutically or veterinarily acceptable salt thereof in the manufacture of a medicament for protecting animals, which may be human or non-human, from damage by parasites selected from the group consisting of acarids, helminths and insects.

In the above, the anthelmintic, acaricidal and insecticidal uses include:

(i) veterinary applications, especially against helminths, acarids or insects which are parasitic on mammals, particularly against fleas, and most particularly against cat fleas (*Ctenocephalides felis*) and dog fleas (*Ctenocephalides canis*);

(ii) agricultural applications, in which harmful insects which damage agricultural crops are eliminated;

(iii) applications against harmful wood eating insects such as termites; and (iv) prophylactic and therapeutic applications against insects which are harmful to human beings.

DETAILED DESCRIPTION OF THE INVENTION

The alkyl groups in the definition of $R^2$ and the alkyl groups which are optional substituents on an amino group in the definition of Substituents A and B are straight or branched alkyl groups having from 1 to 6 carbon atoms, examples of which include include methyl, ethyl, propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethyl-butyl, 1,1-dimethylbutyl, 1,2-dimethylbutyl, 1,3-dimethylbutyl, 2,3-dimethylbutyl and 2-ethylbutyl groups. Alkyl groups having from 1 to 3 carbon atoms are preferred, and methyl groups are most preferred.

The alkanoyl groups which may optionally be substituted with 1, 2 or 3 of substituents A in the defintion of $R^3$ and the alkanoyl groups which are optional substituents on an amino group in the definition of Substituents A and B are straight or branched alkanoyl groups having from 1 to 6 carbon atoms, examples of which include formyl, acetyl, propionyl, butyryl, isobutyryl, valeryl, isovaleryl, pivaloyl and hexanoyl groups. Alkanoyl groups having from 1 to 4 carbon atoms are preferred and acetyl groups are particularly preferred.

The alkenoyl groups which may optionally be substituted with 1 or 2 of substituents A in the defintion of $R^3$ are straight or branched alkenoyl groups having from 3 to 5 carbon atoms. Examples of these groups include propenoyl, butenoyl and pentenoyl groups, of which 4-pentenoyl groups are particularly preferred.

The alkynoyl groups which may optionally be substituted with 1 or 2 of substituents A in the defintion of $R^3$ are straight or branched alkynoyl groups having from 3 to 5 carbon atoms. Examples of these groups include propynoyl, butynoyl and pentynoyl groups, of which 4-pentynoyl groups are particularly preferred.

The alkylsulfonyl groups in the definition of $R^3$ and the alkylsulfonyl groups which are optional substituents on an amino group in the definition of Substituents A and B are straight or branched alkylsulfonyl groups having from 1 to 6 carbon atoms, examples of which include methanesulfonyl, ethanesulfonyl, propanesulfonyl, isopropanesulfonyl, butanesulfonyl group, pentanesulfonyl groups and hexanesulfonyl groups. Of these, alkylsulfonyl groups having from 1 to 3 carbon atoms are preferred, and methanesulfonyl groups are particularly preferred.

The alkoxy groups in the definition of Substituents A and B are straight or branched alkoxy groups having 1 to 6 carbon atoms, examples of which include methoxy, ethoxy, propoxy, isopropoxy, butoxy, pentyloxy and hexyloxy groups. Of these, alkoxy groups having from 1 to 4 carbon atoms are preferred, and methoxy groups are particularly preferred.

The alkoxycarbonyl groups in the definition of $R^3$ and the alkoxycarbonyl groups which are optional substituents on an amino group in the definition of Substituents A and B are carbonyl groups which are substituted with an alkoxy group having from 1 to 6 carbon atoms, examples of which include methoxycarbonyl, ethoxycarbonyl, propoxycarbonyl, isopropoxycarbonyl, butoxycarbonyl, s-butoxycarbonyl, t-butoxycarbonyl, isobutoxycarbonyl groups, pentyloxycarbonyl groups and hexyloxycarbonyl groups. Of these, alkoxycarbonyl groups in which the alkoxy moiety has from 1 to 4 carbon atoms are preferred, and methoxycarbonyl groups are particularly preferred.

Where $R^2$ and $R^3$ together with the nitrogen atom to which they are attached represent a saturated heterocyclic group or where Substituent A represents a saturated heterocyclic group, this group is a 4- to 6-membered heterocyclic ring group containing one ring nitrogen atom and optionally containing one further ring heteroatom selected from the group consisting of sulfur atoms, oxygen atoms and nitrogen atoms, said saturated heterocyclic ring optionally being substituted with 1 or 2 substituents independently selected from Substituents B. Examples of such groups include azetidinyl, pyrrolidinyl, pyrrolinyl, imidazolidinyl, pyrazolidinyl, oxazolidinyl, thiazolidinyl, piperidyl, piperazinyl, morpholinyl and thiomorpholinyl groups. Of these, we prefer azetidinyl, pyrrolidinyl, oxazolidinyl and piperidinyl groups. Where $R^2$ and $R^3$ together with the nitrogen atom to which they are attached represent a saturated heterocyclic group, we particularly prefer pyrrolidin-1-yl and oxazolidin-1-yl groups. Where Substituent A represents a saturated heterocyclic group, we particularly prefer pyrrolidinyl groups.

Where $R^2$ and $R^3$ together with the nitrogen atom to which they are attached represent a saturated heterocyclic group or where Substituent A represents a saturated heterocyclic group as defined and exemplified above, these groups may optionally be substituted with 1 or 2 substituents independently selected from Substituents B. Of these Substituents B, we particularly prefer oxo groups. Example of such substituted saturated heterocyclic groups include azetidinonyl, 2-pyrrolidinonyl, 2-oxazolidinonyl and 2-piperidinonyl groups. Where $R^2$ and $R^3$ together with the nitrogen atom to which they are attached represent a saturated heterocyclic group susbtituted with an oxo group, we particularly prefer preferably 2-pyrrolidinon-1-yl and 2-oxazolidinon-3-yl groups. Where Substituent A represents a saturated heterocyclic group susbstituted with an oxo group, we particularly prefer 2-oxopyrrolidinyl groups.

Where the moiety -a- together with the carbon atom to which it is attached represents a cycloalkyl group, this is a 3- to 6-membered cycloalkyl group, examples of which are cyclopropyl, cyclobutyl, cyclopentyl and cyclohexyl groups. Of these, we prefer 4- or 5-membered cycycloalkyl groups, and we particularly prefer cyclopentyl groups.

Where Substituent A or Substituent B represents a halogen atom, examples include fluorine, chlorine, bromine and iodine atoms, of which we particularly prefer fluorine atoms.

Where Substituent A or Substituent B represents an alkylthio group, this is a straight or branched alkylthio group having 1 to 6 carbon atoms, examples of which include methylthio, ethylthio, propylthio, isopropylthio, butylthio, pentylthio and hexylthio groups. Of these, we prefer alkylthio groups having from 1 to 3 carbon atoms, and we particularly prefer methylthio groups.

Where Substituent A or Substituent B represents an alkanoyloxy group, this is an oxygen atom which is substituted with a straight or branched alkanoyl group having from 1 to 6 carbon atoms as defined and exemplified above. Examples of such alkanoyloxy groups include formyloxy, acetyloxy, propionyloxy, butyryloxy and isobutyryloxy groups, of which we prefer acetyloxy groups.

Where Substituent A or Substituent B represents an amino group substituted with 1 or 2 substituents, preferred examples include amino groups substituted with 1 or 2 substituents selected from the group consisting of alkyl groups having from 1 to 3 carbon atoms, alkanoyl groups having from 1 to 4 carbon atoms, alkylsulfonyl groups having from 1 to 3 carbon atoms and alkoxycarbonyl groups having from 2 to 5 carbon atoms. Of these substituted amino groups, we particularly prefer acetylamino, N-methanesulfonylamino, N-methoxycarbonylamino and N-acetyl-N-methylamino groups.

The compounds of formula (I) of the present invention may be converted to an agriculturally, horticulturally, pharmaceutically or veterinarily acceptable salt thereof by a conventional treatment with a corresponding acid, and these salts also form a part of the present invention. For example, a compound of formula (I) may be treated with an acid in a solvent (for example an ether, ester or alcohol, preferably an ether or alcohol such as diethyl ether or methanol) for 1 to 30 minutes at room temperature, followed by filtration or concentration of the reaction mixture to afford the corresponding salt. Examples of such salts include inorganic acid salts such as hydrohalogenated acid salts (e.g. hydrochlorides, hydrobromides and hydroiodides), nitrates, perchlorates, sulfates and phosphates; organic acid salts such as lower alkanesulfonates (e.g. methanesulfonates, trifluoromethanesulfonates and ethanesulfonates), arylsulfonates (e.g. benzenesulfonates and p-toluenesulfonates), acetates, propionates, butyrates, malates, fumarates, succinates, citrates, ascorbates, tartrates, oxalates and maleates; and amino acid salts such as glycine salts, lysine salts, arginine salts, ornithine salts, glutamates and aspartates.

A salt of a compound of formula (I) of the present invention is an agriculturally, horticulturally, pharmaceutically or veterinarily acceptable salt if it is not unacceptably less active than the free compound of formula (I) and is not unacceptably more toxic than the free compound of formula (I). This can be determined easily by comparative activity and toxicity tests with the free compound of formula (I)

The compounds of formula (1) of the present invention and the salts thereof have asymmetric carbons and they therefore exist as optical isomers. For the compounds of the present invention, each of said isomers and mixture of said isomers are depicted by a single formula, i.e. the formula (I). Accordingly, the present invention covers both the individual isomers and mixtures thereof in any proportion, including racemic mixtures. Specific stereoisomers of the compounds of formula (I) may be prepared by conventional techniques using an optically-active starting material or may be isolated by a conventional optical resolution method from a mixture of stereoisomers obtained by a non-stereospecific synthetic route.

The compounds of formula (I) of the present invention and salts thereof can sometimes take up water upon exposure to the atmosphere or when recrystallized to absorb water or to form a hydrate and such hydrates are also included within the scope of the present invention. Additionally, certain other solvents may be taken up by the compounds of the present invention to produce solvates, which also form a part of the present invention.

Preferred classes of compounds of the present invention are those compounds of formula (I) and agriculturally, horticulturally, pharmaceutically or veterinarily acceptable salts thereof wherein:

(A) $R^1$ is a methyl group or an ethyl group;

(B) $R^2$ is a hydrogen atom or an alkyl group having from 1 to 3 carbon atoms;

(C) $R^2$ is a hydrogen atom or a methyl group;

(D) $R^2$ is a hydrogen atom;

(E) $R^3$ is a hydrogen atom, an alkanoyl group having from 1 to 4 carbon atoms which may optionally be substituted with 1, 2 or 3 substituents independently selected from the group consisting of halogen atoms, cyano groups, hydroxy groups, alkoxy groups having from 1 to 3 carbon atoms, alkylthio groups having from 1 to 3 carbon atoms, alkanoyloxy groups having from 1 to 4 carbon atoms, amino groups which may optionally be substituted with 1 or 2 substituents selected from the group consisting of alkyl groups having from 1 to 3 carbon atoms, alkanoyl groups having from 1 to 4 carbon atoms, alkylsulfonyl groups in which the alkyl moiety has from 1 to 3 carbons and alkoxycarbonyl groups in which the alkoxy moiety has from 1 to 4 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with an oxo group, an alkynoyl group having from 3 to 5 carbon atoms, an alkylsulfonyl group in which the alkyl moiety has from 1 to 3 carbon atoms, or an alkoxycarbonyl group in which the alkoxy group has from 2 to 5 carbon atoms;

(F) $R^3$ is a hydrogen atom or an acetyl group which is optionally substituted with a substituent selected from the group consisting of halogen atoms, cyano groups, hydroxy groups, alkoxy groups having from 1 to 3 carbon atoms, alkylthio groups having from 1 to 3 carbon atoms, alkanoyloxy groups having from 1 to 4 carbon atoms, amino groups, amino groups substituted with 1 or 2 substituents selected from the group consisting of alkyl groups having from 1 to 3 carbon atoms, alkanoyl groups having from 1 to 4 carbon atoms, alkylsulfonyl groups in which the alkyl moiety has from 1 to 3 carbons and alkoxycarbonyl groups in which the alkoxy moiety has from 1 to 4 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with an oxo group;

(G) $R^3$ is a hydrogen atom, an acetyl group, a hydroxyacetyl group, a methoxyacetyl group, an ethoxyacetyl group or a trifluoroacetyl group;

(H) $R^3$ is a methoxyacetyl group;

(I) $R^2$ and $R^3$ together with the nitrogen atom to which they are attached form a saturated 4- to 6-membered heterocyclic ring group containing one ring nitrogen atom and optionally containing one further ring heteroatom selected from the group consisting of sulfur atoms, oxygen atoms and nitrogen atoms, said saturated heterocyclic ring optionally being substituted with an oxo group;

(J) $R^2$ and $R^3$ together with the nitrogen atom to which they are attached form a 2-pyrrolidinon-1-yl group or 2-oxazolidinon-3-yl group;

(K) $R^2$ and $R^3$ together with the nitrogen atom to which they are attached form a 2-oxazolidinon-3-yl group;

(L) the moiety -a- together with the carbon atom to which it is attached form a cyclobutyl group or a cyclopentyl group;

(M) the moiety -a- together with the carbon atom to which it is attached form a cyclopentyl group.

Compounds of formula (I) wherein $R^2$ is selected from (B) above are preferable, from (C) are more preferable and from (D) are most preferable.

Compounds of formula (I) wherein $R^3$ is selected from (E) above are preferable, from (F) are more preferable, from (G) are yet more preferable and from (H) are most preferable.

In compounds of formula (I) wherein $R^2$ and $R^3$ together with the nitrogen atom to which they are attached form a saturated heterocyclic group, compounds wherein $R^2$ and $R^3$ together with the nitrogen atom to which they are attached are as set out in (I) are preferable, in (J) are more preferable and in (K) are most preferable.

Preferred compounds are those wherein $R^1$ is as defined in (A) above, $R^2$ and $R^3$ together with the nitrogen atom to which they are attached are as defined in (I) above and the moiety -a- together with the carbon atom to which it is attached are as defined in (L) above.

More preferred compounds are those wherein $R^1$ is as defined in (A) above, $R^2$ and $R^3$ together with the nitrogen atom to which they are attached are as defined in (J) above and the moiety -a- together with the carbon atom to which it is attached are as defined in (M) above.

Most preferred compounds are those wherein $R^1$ is as defined in (A) above, $R^2$ and $R^3$ together with the nitrogen atom to which they are attached are as defined in (K) above and the moiety -a- together with the carbon atom to which it is attached are as defined in (M) above.

Preferred compounds are those wherein $R^1$ is as defined in (A) above, $R^2$ is as defined in (B) above, $R^3$ is as defined in (E) above and the moiety -a- together with the carbon atom to which it is attached are as defined in (L) above.

More preferred compounds are those wherein $R^1$ is as defined in (A) above, $R^2$ is as defined in (C) above, $R^3$ is as defined in (F) above and the moiety -a- together with the carbon atom to which it is attached are as defined in (M) above.

Yet more preferred compounds are those wherein $R^1$ is as defined in (A) above, $R^2$ is as defined in (D) above, $R^3$ is as defined in (G) above and the moiety -a- together with the carbon atom to which it is attached are as defined in (M) -above.

Most preferred compounds are those wherein $R^1$ is as defined in (A) above, $R^2$ is as defined in (D) above, $R^3$ is as defined in (H) above and the moiety -a- together with the carbon atom to which it is attached are as defined in (M) above.

The following table is intended to illustrate representative compounds of the present invention and is not intended to limit the scope of this invention.

In the following Table 1, the following abbreviations are used:

TABLE 1

| Compound number | $R^1$ | $R^2$ | $R^3$ | -a- |
|---|---|---|---|---|
| 1 | Et | H | H | —$(CH_2)_4$— |
| 2 | Et | H | MeCO | —$(CH_2)_4$— |
| 3 | Et | H | $CF_3CO$ | —$(CH_2)_4$— |
| 4 | Et | H | $ClCH_2CO$ | —$(CH_2)_4$— |
| 5 | Et | H | $BrCH_2CO$ | —$(CH_2)_4$— |
| 6 | Et | H | $NCCH_2CO$ | —$(CH_2)_4$— |
| 7 | Et | H | $HOCH_2CO$ | —$(CH_2)_4$— |
| 8 | Et | H | $MeOCH_2CO$ | —$(CH_2)_4$— |
| 9 | Et | H | $EtOCH_2CO$ | —$(CH_2)_4$— |
| 10 | Et | H | $PrOCH_2CO$ | —$(CH_2)_4$— |
| 11 | Et | H | $iPrOCH_2CO$ | —$(CH_2)_4$— |
| 12 | Et | H | $MeSCH_2CO$ | —$(CH_2)_4$— |
| 13 | Et | H | $EtSCH_2CO$ | —$(CH_2)_4$— |
| 14 | Et | H | $PrSCH_2CO$ | —$(CH_2)_4$— |
| 15 | Et | H | $iPrSCH_2CO$ | —$(CH_2)_4$— |
| 16 | Et | H | $MeCOOCH_2CO$ | —$(CH_2)_4$— |
| 17 | Et | H | $EtCOOCH_2CO$ | —$(CH_2)_4$— |
| 18 | Et | H | $PrCOOCH_2CO$ | —$(CH_2)_4$— |
| 19 | Et | H | $iPrCOOCH_2CO$ | —$(CH_2)_4$— |
| 20 | Et | H | $MeSO_2$ | —$(CH_2)_4$— |
| 21 | Et | H | $EtSO_2$ | —$(CH_2)_4$— |
| 22 | Et | H | $PrSO_2$ | —$(CH_2)_4$— |
| 23 | Et | H | $iPrSO_2$ | —$(CH_2)_4$— |
| 24 | Et | H | MeOCO | —$(CH_2)_4$— |
| 25 | Pt | H | EtOCO | —$(CH_2)_4$— |
| 26 | Et | H | PrOCO | —$(CH_2)_4$— |
| 27 | Et | H | iPrOCO | —$(CH_2)_4$— |
| 28 | Et | H | BuOCO | —$(CH_2)_4$— |
| 29 | Et | H | iBuOCO | —$(CH_2)_4$— |
| 30 | Et | H | sBuOCO | —$(CH_2)_4$— |
| 31 | Et | H | tBuOCO | —$(CH_2)_4$— |
| 32 | Et | Me | MeCO | —$(CH_2)_4$— |
| 33 | Et | Me | $CF_3CO$ | —$(CH_2)_4$— |
| 34 | Et | Me | $HOCH_2CO$ | —$(CH_2)_4$— |
| 35 | Et | Me | $MeOCH_2CO$ | —$(CH_2)_4$— |
| 36 | Et | Me | $MeSCH_2CO$ | —$(CH_2)_4$— |
| 37 | Et | Me | $MeCOOCH_2CO$ | —$(CH_2)_4$— |
| 38 | Et | Me | $MeSO_2$ | —$(CH_2)_4$— |
| 39 | Et | Me | MeOCO | —$(CH_2)_4$— |
| 40 | Et | ($R^2R^3N$): 2-azetidinon-1-yl | | —$(CH_2)_4$— |
| 41 | Et | ($R^2R^3N$): 2-pyrrolidinon-1-yl | | —$(CH_2)_4$— |
| 42 | Et | ($R^2R^3N$): 2-oxazolidon-3-yl | | —$(CH_2)_4$— |
| 43 | Et | ($R^2R^3N$): 2-piperidinon-1-yl | | —$(CH_2)_4$— |
| 44 | Me | H | H | —$(CH_2)_4$— |
| 45 | Me | H | MeCO | —$(CH_2)_4$— |
| 46 | Me | H | $CF_3CO$ | —$(CH_2)_4$— |
| 47 | Me | H | $ClCH_2CO$ | —$(CH_2)_4$— |
| 48 | Me | H | $BrCH_2CO$ | —$(CH_2)_4$— |
| 49 | Me | H | $NCCH_2CO$ | —$(CH_2)_4$— |
| 50 | Me | H | $HOCH_2CO$ | —$(CH_2)_4$— |
| 51 | Me | H | $MeOCH_2CO$ | —$(CH_2)_4$— |
| 52 | Me | H | $EtOCH_2CO$ | —$(CH_2)_4$— |
| 53 | Me | H | $PrOCH_2CO$ | —$(CH_2)_4$— |
| 54 | Me | H | $iPrOCH_2CO$ | —$(CH_2)_4$— |
| 55 | Me | H | $MeSCH_2CO$ | —$(CH_2)_4$— |
| 56 | Me | H | $EtSCH_2CO$ | —$(CH_2)_4$— |
| 57 | Me | H | $PrSCH_2CO$ | —$(CH_2)_4$— |
| 58 | Me | H | $iPrSCH_2CO$ | —$(CH_2)_4$— |
| 59 | Me | H | $MeCOOCH_2CO$ | —$(CH_2)_4$— |
| 60 | Me | H | $EtCOOCH_2CO$ | —$(CH_2)_4$— |
| 61 | Me | H | $PrCOOCH_2CO$ | —$(CH_2)_4$— |
| 62 | Me | H | $iPrCOOCH_2CO$ | —$(CH_2)_4$— |
| 63 | Me | H | $MeSO_2$ | —$(CH_2)_4$— |
| 64 | Me | H | $EtSO_2$ | —$(CH_2)_4$— |
| 65 | Me | H | $PrSO_2$ | —$(CH_2)_4$— |
| 66 | Me | H | $iPrSO_2$ | —$(CH_2)_4$— |
| 67 | Me | H | MeOCO | —$(CH_2)_4$— |
| 68 | Me | H | EtOCO | —$(CH_2)_4$— |
| 69 | Me | H | PrOCO | —$(CH_2)_4$— |
| 70 | Me | H | iPrOCO | —$(CH_2)_4$— |
| 71 | Me | H | BuOCO | —$(CH_2)_4$— |
| 72 | Me | H | iBuOCO | —$(CH_2)_4$— |
| 73 | Me | H | sBuOCO | —$(CH_2)_4$— |
| 74 | Me | H | tBuOCO | —$(CH_2)_4$— |
| 75 | Me | Me | MeCO | —$(CH_2)_4$— |
| 76 | Me | Me | $CF_3CO$ | —$(CH_2)_4$— |
| 77 | Me | Me | $HOCH_2CO$ | —$(CH_2)_4$— |
| 78 | Me | Me | $MeOCH_2CO$ | —$(CH_2)_4$— |
| 79 | Me | Me | $MeSCH_2CO$ | —$(CH_2)_4$— |
| 80 | Me | Me | $MeCOOCH_2CO$ | —$(CH_2)_4$— |
| 81 | Me | Me | $MeSO_2$ | —$(CH_2)_4$— |
| 82 | Me | Me | MeOCO | —$(CH_2)_4$— |
| 83 | Me | ($R^2R^3N$): 2-azetidinon-1-yl | | —$(CH_2)_4$— |
| 84 | Me | ($R^2R^3N$): 2-pyrrolidinon-1-yl | | —$(CH_2)_4$— |
| 85 | Me | ($R^2R^3N$): 2-oxazolidon-3-yl | | —$(CH_2)_4$— |
| 86 | Me | ($R^2R^3N$): 2-piperidinon-1-yl | | —$(CH_2)_4$— |
| 87 | iPr | H | H | —$(CH_2)_4$— |
| 88 | iPr | H | MeCO | —$(CH_2)_4$— |
| 89 | iPr | H | $CF_3CO$ | —$(CH_2)_4$— |
| 90 | iPr | H | $ClCH_2CO$ | —$(CH_2)_4$— |
| 91 | iPr | H | $BrCH_2CO$ | —$(CH_2)_4$— |
| 92 | iPr | H | $NCCH_3CO$ | —$(CH_2)_4$— |
| 93 | iPr | H | $HOCH_2CO$ | —$(CH_2)_4$— |
| 94 | iPr | H | $MeOCH_2CO$ | —$(CH_2)_4$— |
| 95 | iPr | H | $EtOCH_2CO$ | —$(CH_2)_4$— |

TABLE 1-continued

| Compound number | R¹ | R² | R³ | -a- |
|---|---|---|---|---|
| 96 | iPr | H | PrOCH₂CO | —(CH₂)₄— |
| 97 | iPr | H | iPrOCH₂CO | —(CH₂)₄— |
| 98 | iPr | H | MeSCH₂CO | —(CH₂)₄— |
| 99 | iPr | H | EtSCH₂CO | —(CH₂)₄— |
| 100 | iPr | H | PrSCH₂CO | —(CH₂)₄— |
| 101 | iPr | H | iPrSCH₂CO | —(CH₂)₄— |
| 102 | iPr | H | MeCOOCH₂CO | —(CH₂)₄— |
| 103 | iPr | H | EtCOOCH₂CO | —(CH₂)₄— |
| 104 | iPr | H | PrCOOCH₂CO | —(CH₂)₄— |
| 105 | iPr | H | iPrCOOCH₂CO | —(CH₂)₄— |
| 106 | iPr | H | MeSO₂ | —(CH₂)₄— |
| 107 | iPr | H | EtSO₂ | —(CH₂)₄— |
| 108 | iPr | H | PrSO₂ | —(CH₂)₄— |
| 109 | iPr | H | iPrSO₂ | —(CH₂)₄— |
| 110 | iPr | H | MeOCO | —(CH₂)₄— |
| 111 | iPr | H | EtOCO | —(CH₂)₄— |
| 112 | iPr | H | PrOCO | —(CH₂)₄— |
| 113 | iPr | H | iPrOCO | —(CH₂)₄— |
| 114 | iPr | H | BuOCO | —(CH₂)₄— |
| 115 | iPr | H | iBuOCO | —(CH₂)₄— |
| 116 | iPr | H | sBuOCO | —(CH₂)₄— |
| 117 | iPr | H | tBuOCO | —(CH₂)₄— |
| 118 | iPr | Me | MeCO | —(CH₂)₄— |
| 119 | iPr | Me | CF₃CO | —(CH₂)₄— |
| 120 | iPr | Me | HOCH₂CO | —(CH₂)₄— |
| 121 | iPr | Me | MeOCH₂CO | —(CH₂)₄— |
| 122 | iPr | Me | MeSCH₂CO | —(CH₂)₄— |
| 123 | iPr | Me | MeCOOCH₂CO | —(CH₂)₄— |
| 124 | iPr | Me | MeSO₂ | —(CH₂)₄— |
| 125 | iPr | Me | MeOCO | —(CH₂)₄— |
| 126 | iPr | (R²R³N): 2-azetidinon-1-yl | | —(CH₂)₄— |
| 127 | iPr | (R²R³N): 2-pyrrolidinon-1-yl | | —(CH₂)₄— |
| 128 | iPr | (R²R³N): 2-oxazolidon-3-yl | | —(CH₂)₄— |
| 129 | iPr | (R²R³N): 2-piperidinon-1-yl | | —(CH₂)₄— |
| 130 | sBu | H | H | —(CH₂)₄— |
| 131 | sBu | H | MeCO | —(CH₂)₄— |
| 132 | sBu | H | CF₃CO | —(CH₂)₄— |
| 133 | sBu | H | ClCH₂CO | —(CH₂)₄— |
| 134 | sBu | H | BrCH₂CO | —(CH₂)₄— |
| 135 | sBu | H | NCCH₂CO | —(CH₂)₄— |
| 136 | sBu | H | HOCH₂CO | —(CH₂)₄— |
| 137 | sBu | H | MeOCH₂CO | —(CH₂)₄— |
| 138 | sBu | H | EtOCH₂CO | —(CH₂)₄— |
| 139 | sBu | H | PrOCH₂CO | —(CH₂)₄— |
| 140 | sBu | H | iPrOCH₂CO | —(CH₂)₄— |
| 141 | sBu | H | MeSCH₂CO | —(CH₂)₄— |
| 142 | sBu | H | EtSCH₂CO | —(CH₂)₄— |
| 143 | sBu | H | PrSCH₂CO | —(CH₂)₄— |
| 144 | sBu | H | iPrSCH₂CO | —(CH₂)₄— |
| 145 | sBu | H | MeCOOCH₂CO | —(CH₂)₄— |
| 146 | sBu | H | EtCOOCH₂CO | —(CH₂)₄— |
| 147 | sBu | H | PrCOOCH₂CO | —(CH₂)₄— |
| 148 | sBu | H | iPrCOOCH₂CO | —(CH₂)₄— |
| 149 | sBu | H | MeSO₂ | —(CH₂)₄— |
| 150 | sBu | H | EtSO₂ | —(CH₂)₄— |
| 151 | sBu | H | PrSO₂ | —(CH₂)₄— |
| 152 | sBu | H | iPrSO₂ | —(CH₂)₄— |
| 153 | sBu | H | MeOCO | —(CH₂)₄— |
| 154 | sBu | H | EtOCO | —(CH₂)₄— |
| 155 | sBu | H | PrOCO | —(CH₂)₄— |
| 156 | sBu | H | iPrOCO | —(CH₂)₄— |
| 157 | sBu | H | BuOCO | —(CH₂)₄— |
| 158 | sBu | H | iBuOCO | —(CH₂)₄— |
| 159 | sBu | H | sBuOCO | —(CH₂)₄— |
| 160 | sBu | H | tBuOCO | —(CH₂)₄— |
| 161 | sBu | Me | MeCO | —(CH₂)₄— |
| 162 | sBu | Me | CF₃CO | —(CH₂)₄— |
| 163 | sBu | Me | HOCH₂CO | —(CH₂)₄— |
| 164 | sBu | Me | MeOCH₂CO | —(CH₂)₄— |
| 165 | sBu | Me | MeSCH₂CO | —(CH₂)₄— |
| 166 | sBu | Me | MeCOOCH₂CO | —(CH₂)₄— |
| 167 | sBu | Me | MeSO₂ | —(CH₂)₄— |
| 168 | sBu | Me | MeOCO | —(CH₂)₄— |
| 169 | sBu | (R²R³N): 2-azetidinon-1-yl | | —(CH₂)₄— |
| 170 | sBu | (R²R³N): 2-pyrrolidinon-1-yl | | —(CH₂)₄— |
| 171 | sBu | (R²R³N): 2-oxazolidon-3-yl | | —(CH₂)₄— |
| 172 | sBu | (R²R³N): 2-piperidinon-1-yl | | —(CH₂)₄— |
| 173 | Et | H | H | —(CH₂)₃— |
| 174 | Et | H | MeCO | —(CH₂)₃— |
| 175 | Et | H | CF₃CO | —(CH₂)₃— |
| 176 | Et | H | ClCH₂CO | —(CH₂)₃— |
| 177 | Et | H | BrCH₂CO | —(CH₂)₃— |
| 178 | Et | H | NCCH₂CO | —(CH₂)₃— |
| 179 | Et | H | HOCH₂CO | —(CH₂)₃— |
| 180 | Et | H | MeOCH₂CO | —(CH₂)₃— |
| 181 | Et | H | EtOCH₂CO | —(CH₂)₃— |
| 182 | Et | H | PrOCH₂CO | —(CH₂)₃— |
| 183 | Et | H | iPrOCH₂CO | —(CH₂)₃— |
| 184 | Et | H | MeSCH₂CO | —(CH₂)₃— |
| 185 | Et | H | EtSCH₂CO | —(CH₂)₃— |
| 186 | Et | H | PrSCH₂CO | —(CH₂)₃— |
| 187 | Et | H | iPrSCH₂CO | —(CH₂)₃— |
| 188 | Et | H | MeCOOCH₂CO | —(CH₂)₃— |
| 189 | Et | H | EtCOOCH₂CO | —(CH₂)₃— |
| 190 | Et | H | PrCOOCH₂CO | —(CH₂)₃— |
| 191 | Et | H | iPrCOOCH₂CO | —(CH₂)₃— |
| 192 | Et | H | MeSO₂ | —(CH₂)₃— |
| 193 | Et | H | EtSO₂ | —(CH₂)₃— |
| 194 | Et | H | PrSO₂ | —(CH₂)₃— |
| 195 | Et | H | iPrSO₂ | —(CH₂)₃— |
| 196 | Et | H | MeOCO | —(CH₂)₃— |
| 197 | Et | H | EtOCO | —(CH₂)₃— |
| 198 | Et | H | PrOCO | —(CH₂)₃— |
| 199 | Et | H | iPrOCO | —(CH₂)₃— |
| 200 | Et | H | BuOCO | —(CH₂)₃— |
| 201 | Et | H | iBuOCO | —(CH₂)₃— |
| 202 | Et | H | sBuOCO | —(CH₂)₃— |
| 203 | Et | H | tBuOCO | —(CH₂)₃— |
| 204 | Et | Me | MeCO | —(CH₂)₃— |
| 205 | Et | Me | CF₃CO | —(CH₂)₃— |
| 206 | Et | Me | HOCH₂CO | —(CH₂)₃— |
| 207 | Et | Me | MeOCH₂CO | —(CH₂)₃— |
| 208 | Et | Me | MeSCH₂CO | —(CH₂)₃— |
| 209 | Et | Me | MeCOOCH₂CO | —(CH₂)₃— |
| 210 | Et | Me | MeSO₂ | —(CH₂)₃— |
| 211 | Et | Me | MeOCO | —(CH₂)₃— |
| 212 | Et | (R²R³N): 2-azetidinon-1-yl | | —(CH₂)₃— |
| 213 | Et | (R²R³N): 2-pyrrolidinon-1-yl | | —(CH₂)₃— |
| 214 | Et | (R²R³N): 2-oxazolidon-3-yl | | —(CH₂)₃— |
| 215 | Et | (R²R³N): 2-piperidinon-1-yl | | —(CH₂)₃— |
| 216 | Me | H | H | —(CH₂)₃— |
| 217 | Me | H | MeCO | —(CH₂)₃— |
| 218 | Me | H | CF₃CO | —(CH₂)₃— |
| 219 | Me | H | ClCH₂CO | —(CH₂)₃— |
| 220 | Me | H | BrCH₂CO | —(CH₂)₃— |
| 221 | Me | H | NCCH₂CO | —(CH₂)₃— |
| 222 | Me | H | HOCH₂CO | —(CH₂)₃— |
| 223 | Me | H | MeOCH₂CO | —(CH₂)₃— |
| 224 | Me | H | EtOCH₂CO | —(CH₂)₃— |
| 225 | Me | H | PrOCH₂CO | —(CH₂)₃— |
| 226 | Me | H | iPrOCH₂CO | —(CH₂)₃— |
| 227 | Me | H | MeSCH₂CO | —(CH₂)₃— |
| 228 | Me | H | EtSCH₂CO | —(CH₂)₃— |
| 229 | Me | H | PrSCH₂CO | —(CH₂)₃— |
| 230 | Me | H | iPrSCH₂CO | —(CH₂)₃— |
| 231 | Me | H | MeCOOCH₂CO | —(CH₂)₃— |
| 232 | Me | H | EtCOOCH₂CO | —(CH₂)₃— |
| 233 | Me | H | PrCOOCH₂CO | —(CH₂)₃— |
| 234 | Me | H | iPrCOOCH₂CO | —(CH₂)₃— |
| 235 | Me | H | MeSO₂ | —(CH₂)₃— |
| 236 | Me | H | EtSO₂ | —(CH₂)₃— |
| 237 | Me | H | PrSO₂ | —(CH₂)₃— |
| 238 | Me | H | iPrSO₂ | —(CH₂)₃— |
| 239 | Me | H | MeOCO | —(CH₂)₃— |
| 240 | Me | H | EtOCO | —(CH₂)₃— |
| 241 | Me | H | PrOCO | —(CH₂)₃— |
| 242 | Me | H | iPrOCO | —(CH₂)₃— |
| 243 | Me | H | BuOCO | —(CH₂)₃— |
| 244 | Me | H | iBuOCO | —(CH₂)₃— |
| 245 | Me | H | sBuOCO | —(CH₂)₃— |
| 246 | Me | H | tBuOCO | —(CH₂)₃— |
| 247 | Me | Me | MeCO | —(CH₂)₃— |

TABLE 1-continued

| Compound number | $R^1$ | $R^2$ | $R^3$ | -a- |
|---|---|---|---|---|
| 248 | Me | Me | $CF_3CO$ | $-(CH_2)_3-$ |
| 249 | Me | Me | $HOCH_2CO$ | $-(CH_2)_3-$ |
| 250 | Me | Me | $MeOCH_2CO$ | $-(CH_2)_3-$ |
| 251 | Me | Me | $MeSCH_2CO$ | $-(CH_2)_3-$ |
| 252 | Me | Me | $MeCOOCH_2CO$ | $-(CH_2)_3-$ |
| 253 | Me | Me | $MeSO_2$ | $-(CH_2)_3-$ |
| 254 | Me | Me | MeOCO | $-(CH_2)_3-$ |
| 255 | Me | ($R^2R^3N$): 2-azetidinon-1-yl | | $-(CH_2)_3-$ |
| 256 | Me | ($R^2R^3N$): 2-pyrrolidinon-1-yl | | $-(CH_2)_3-$ |
| 257 | Me | ($R^2R^3N$): 2-oxazolidon-3-yl | | $-(CH_2)_3-$ |
| 258 | Me | ($R^2R^3N$): 2-piperidinon-1-yl | | $-(CH_2)_3-$ |
| 259 | iPr | H | H | $-(CH_2)_3-$ |
| 260 | iPr | H | MeCO | $-(CH_2)_3-$ |
| 261 | iPr | H | $CF_3CO$ | $-(CH_2)_3-$ |
| 262 | iPr | H | $ClCH_2CO$ | $-(CH_2)_3-$ |
| 263 | iPr | H | $BrCH_2CO$ | $-(CH_2)_3-$ |
| 264 | iPr | H | $NCCH_2CO$ | $-(CH_2)_3-$ |
| 265 | iPr | H | $HOCH_2CO$ | $-(CH_2)_3-$ |
| 266 | iPr | H | $MeOCH_2CO$ | $-(CH_2)_3-$ |
| 267 | iPr | H | $EtOCH_2CO$ | $-(CH_2)_3-$ |
| 268 | iPr | H | $PrOCH_2CO$ | $-(CH_2)_3-$ |
| 269 | iPr | H | $iPrOCH_2CO$ | $-(CH_2)_3-$ |
| 270 | iPr | H | $MeSCH_2CO$ | $-(CH_2)_3-$ |
| 271 | iPr | H | $EtSCH_2CO$ | $-(CH_2)_3-$ |
| 272 | iPr | H | $PrSCH_2CO$ | $-(CH_2)_3-$ |
| 273 | iPr | H | $iPrSCH_2CO$ | $-(CH_2)_3-$ |
| 274 | iPr | H | $MeCOOCH_2CO$ | $-(CH_2)_3-$ |
| 275 | iPr | H | $EtCOOCH_2CO$ | $-(CH_2)_3-$ |
| 276 | iPr | H | $PrCOOCH_2CO$ | $-(CH_2)_3-$ |
| 277 | iPr | H | $iPrCOOCH_2CO$ | $-(CH_2)_3-$ |
| 278 | iPr | H | $MeSO_2$ | $-(CH_2)_3-$ |
| 279 | iPr | H | $EtSO_2$ | $-(CH_2)_3-$ |
| 280 | iPr | H | $PrSO_2$ | $-(CH_2)_3-$ |
| 281 | iPr | H | $iPrSO_2$ | $-(CH_2)_3-$ |
| 282 | iPr | H | MeOCO | $-(CH_2)_3-$ |
| 283 | iPr | H | EtOCO | $-(CH_2)_3-$ |
| 284 | iPr | H | PrOCO | $-(CH_2)_3-$ |
| 285 | iPr | H | iPrOCO | $-(CH_2)_3-$ |
| 286 | iPr | H | BuOCO | $-(CH_2)_3-$ |
| 287 | iPr | H | iBuOCO | $-(CH_2)_3-$ |
| 288 | iPr | H | sBuOCO | $-(CH_2)_3-$ |
| 289 | iPr | H | tBuOCO | $-(CH_2)_3-$ |
| 290 | iPr | Me | MeCO | $-(CH_2)_3-$ |
| 291 | iPr | Me | $CF_3CO$ | $-(CH_2)_3-$ |
| 292 | iPr | Me | $HOCH_2CO$ | $-(CH_2)_3-$ |
| 293 | iPr | Me | $MeOCH_2CO$ | $-(CH_2)_3-$ |
| 294 | iPr | Me | $MeSCH_2CO$ | $-(CH_2)_3-$ |
| 295 | iPr | Me | $MeCOOCH_2CO$ | $-(CH_2)_3-$ |
| 296 | iPr | Me | $MeSO_2$ | $-(CH_2)_3-$ |
| 297 | iPr | Me | MeOCO | $-(CH_2)_3-$ |
| 298 | iPr | ($R^2R^3N$): 2-azetidinon-1-yl | | $-(CH_2)_3-$ |
| 299 | iPr | ($R^2R^3N$): 2-pyrrolidinon-1-yl | | $-(CH_2)_3-$ |
| 300 | iPr | ($R^2R^3N$): 2-oxazolidon-3-yl | | $-(CH_2)_3-$ |
| 301 | iPr | ($R^2R^3N$): 2-piperidinon-1-yl | | $-(CH_2)_3-$ |
| 302 | sBu | H | H | $-(CH_2)_3-$ |
| 303 | sBu | H | MeCO | $-(CH_2)_3-$ |
| 304 | sBu | H | $CF_3CO$ | $-(CH_2)_3-$ |
| 305 | sBu | H | $ClCH_2CO$ | $-(CH_2)_3-$ |
| 306 | sBu | H | $BrCH_2CO$ | $-(CH_2)_3-$ |
| 307 | sBu | H | $NCCH_2CO$ | $-(CH_2)_3-$ |
| 308 | sBu | H | $HOCH_2CO$ | $-(CH_2)_3-$ |
| 309 | sBu | H | $MeOCH_2CO$ | $-(CH_2)_3-$ |
| 310 | sBu | H | $EtOCH_2CO$ | $-(CH_2)_3-$ |
| 311 | sBu | H | $PrOCH_2CO$ | $-(CH_2)_3-$ |
| 312 | sBu | H | $iPrOCH_2CO$ | $-(CH_2)_3-$ |
| 313 | sBu | H | $MeSCH_2CO$ | $-(CH_2)_3-$ |
| 314 | sBu | H | $EtSCH_2CO$ | $-(CH_2)_3-$ |
| 315 | sBu | H | $PrSCH_2CO$ | $-(CH_2)_3-$ |
| 316 | sBu | H | $iPrSCH_2CO$ | $-(CH_2)_3-$ |
| 317 | sBu | H | $MeCOOCH_2CO$ | $-(CH_2)_3-$ |
| 318 | sBu | H | $EtCOOCH_2CO$ | $-(CH_2)_3-$ |
| 319 | sBu | H | $PrCOOCH_2CO$ | $-(CH_2)_3-$ |
| 320 | sBu | H | $iPrCOOCH_2CO$ | $-(CH_2)_3-$ |
| 321 | sBu | H | $MeSO_2$ | $-(CH_2)_3-$ |
| 322 | sBu | H | $EtSO_2$ | $-(CH_2)_3-$ |
| 323 | sBu | H | $PrSO_2$ | $-(CH_2)_3-$ |
| 324 | sBu | H | $iPrSO_2$ | $-(CH_2)_3-$ |
| 325 | sBu | H | MeOCO | $-(CH_2)_3-$ |
| 326 | sBu | H | EtOCO | $-(CH_2)_3-$ |
| 327 | sBu | H | PrOCO | $-(CH_2)_3-$ |
| 328 | sBu | H | iPrOCO | $-(CH_2)_3-$ |
| 329 | sBu | H | BuOCO | $-(CH_2)_3-$ |
| 330 | sBu | H | iBuOCO | $-(CH_2)_3-$ |
| 331 | sBu | H | sBuOCO | $-(CH_2)_3-$ |
| 332 | sBu | H | tBuOCO | $-(CH_2)_3-$ |
| 333 | sBu | Me | MeCO | $-(CH_2)_3-$ |
| 334 | sBu | Me | $CF_3CO$ | $-(CH_2)_3-$ |
| 335 | sBu | Me | $HOCH_2CO$ | $-(CH_2)_3-$ |
| 336 | sBu | Me | $MeOCH_2CO$ | $-(CH_2)_3-$ |
| 337 | sBu | Me | $MeSCH_2CO$ | $-(CH_2)_3-$ |
| 338 | sBu | Me | $MeCOOCH_2CO$ | $-(CH_2)_3-$ |
| 339 | sBu | Me | $MeSO_2$ | $-(CH_2)_3-$ |
| 340 | sBu | Me | MeOCO | $-(CH_2)_3-$ |
| 341 | sBu | ($R^2R^3N$): 2-azetidinon-1-yl | | $-(CH_2)_3-$ |
| 342 | sBu | ($R^2R^3N$): 2-pyrrolidinon-1-yl | | $-(CH_2)_3-$ |
| 343 | sBu | ($R^2R^3N$): 2-oxazolidon-3-yl | | $-(CH_2)_3-$ |
| 344 | sBu | ($R^2R^3N$): 2-piperidinon-1-yl | | $-(CH_2)_3-$ |
| 345 | Me | H | $MeCON(Me)CH_2CO$ | $-(CH_2)_4-$ |
| 346 | Et | H | $MeCON(Me)CH_2CO$ | $-(CH_2)_4-$ |
| 347 | iPr | H | $MeCON(Me)CH_2CO$ | $-(CH_2)_4-$ |
| 348 | sBu | H | $MeCON(Me)CH_2CO$ | $-(CH_2)_4-$ |
| 349 | Me | H | OPA | $-(CH_2)_4-$ |
| 350 | Et | H | OPA | $-(CH_2)_4-$ |
| 351 | iPr | H | OPA | $-(CH_2)_4-$ |
| 352 | sBu | H | OPA | $-(CH_2)_4-$ |
| 353 | Me | H | Pyl | $-(CH_2)_3-$ |
| 354 | Et | H | Pyl | $-(CH_2)_3-$ |
| 355 | iPr | H | Pyl | $-(CH_2)_3-$ |
| 356 | sBu | H | Pyl | $-(CH_2)_3-$ |
| 357 | Et | H | HCO | $-(CH_2)_4-$ |
| 358 | Et | H | HCO | $-(CH_2)_3-$ |

Bu: butyl group
iBu: isobutyl group
sBu: s-butyl group
tBu: t-butyl group
Et: ethyl group
Me: methyl group
Pr: propyl group
iPr: isopropyl group
OPA: 2-oxopyrrolidin-1-ylacetyl group
Pyl: 4-pentynoyl Preferred compounds of formula (I) of the present invention are compound nos 1, 2, 3, 6, 7, 8, 12, 16, 20, 24, 35, 41, 42, 44, 45, 46, 50, 51, 55, 59, 63, 67, 78, 84, 85, 86, 87, 92, 93, 94, 98, 102, 106, 110, 130, 131, 132, 136, 137, 141, 145, 149, 153, 174, 175, 178, 179, 180, 184, 188, 192, 196, 207, 213, 214, 217, 218, 222, 223, 227, 231, 235, 239, 250, 256, 257, 258, 259, 264, 265, 266, 270, 274, 278, 282, 303, 304, 308, 309, 313, 317, 321, 325, 346, 349 and 353.

More preferred compounds of formula (I) of the present invention are compound nos 1, 2, 6, 7, 8, 12, 16, 20, 24, 35, 42, 44, 45, 46, 50, 51, 55, 59, 63, 67, 174, 175, 179, 180, 184, 188, 192, 196, 217, 218, 222, 223, 227, 231, 235, 239, 346, 349 and 353.

Most preferred compounds of formula (I) of the present invention are compound nos 1, 2, 6, 7, 8, 20, 50, 51, 63, 179, 180, 192, 222, 223, 235 and 346.

Compounds of formula (I) of the present invention may easily be prepared by conventional techniques, for example according to the synthetic procedures shown in the following Reaction Scheme A:

Reaction Scheme A

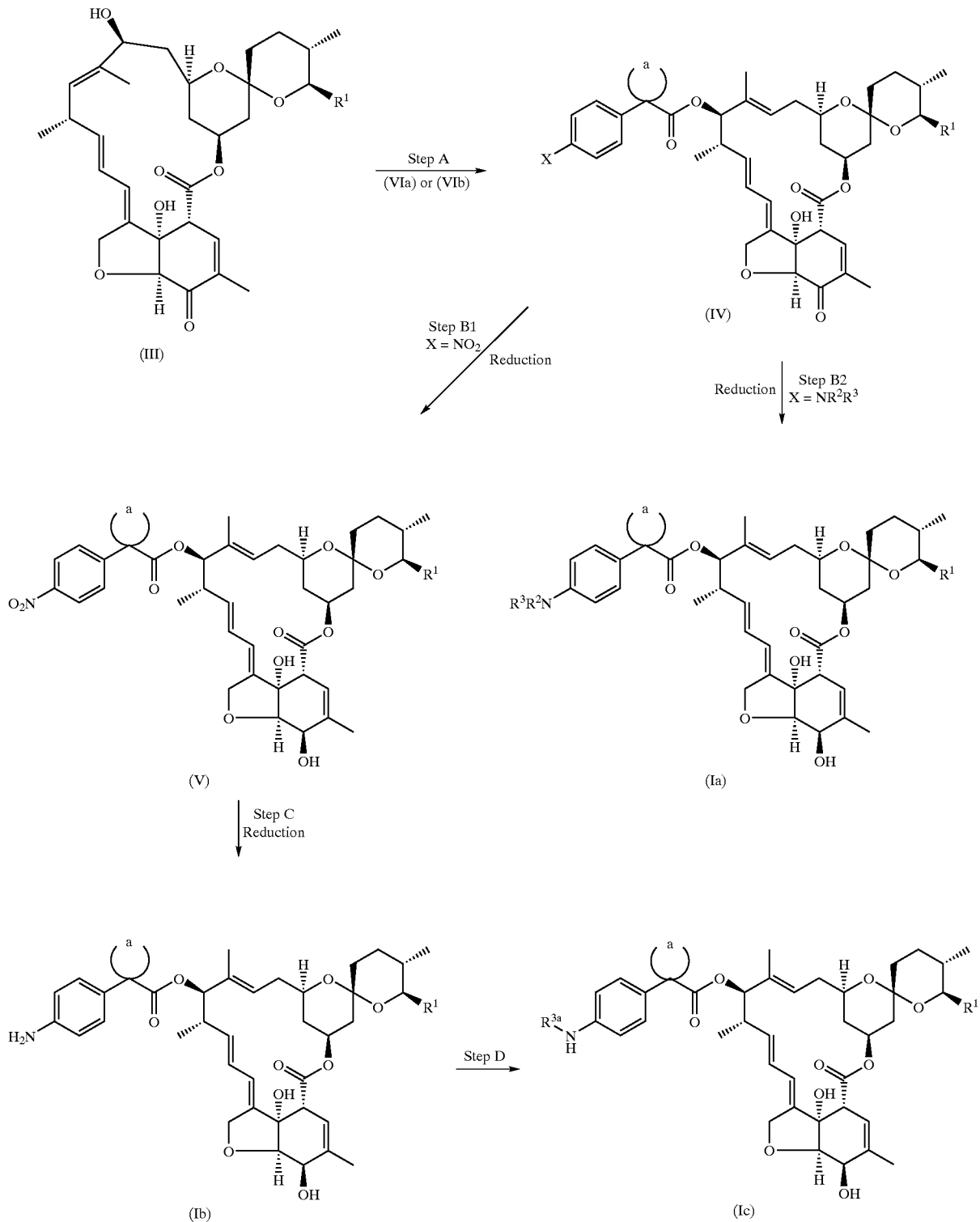

In the above formulae, $R^1$, $R^2$ and -a- are as defined above, X is nitro group or a group of formula $—NR^2R^3$ in which $R^2$ and $R^3$ are as defined above, and $R^{3a}$ is the same as $R^3$ but with the exclusion of hydrogen atoms.

The starting compounds of formula (III) are 15-hydroxymilbemycin derivatives which are well-known in the art. Their production is disclosed, for example, in Japanese patent application publication number Sho-60-158191 and EP-A-0147852.

The starting compounds of formula (VIb) below (wherein $R^2$, $R^3$ and -a- are as defined above) may be prepared by known techniques using the known compounds of formula (VIa) below.

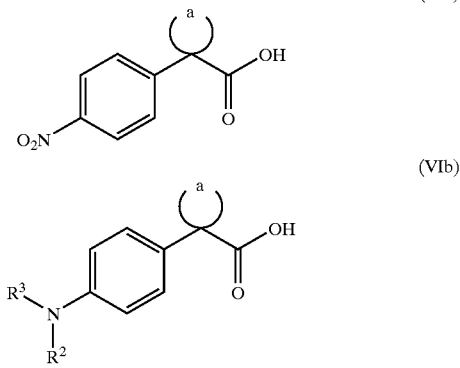

(VIa)

(VIb)

For example, a compound of formula (VIb), in which $R^2$ is an alkyl group and $R^3$ is a group of formula $R^{3a}$ as defined above may be prepared as follows:

First, a compound of formula (VIa) is esterified so as to protect the carboxy group. The resulting esterified compound is then subjected to catalytic reduction to convert the nitro group to an amino group. This amino compound is then either acylated or sulfonylated to convert the amino group to an amide group of formula —$NHR^{3a}$ in which $R^{3a}$ is as defined above. The resulting amide compound is then treated with an alkylating agent such as methyl iodide in the presence of a base such as sodium hydride to convert the group of formula —$NHR^{3a}$ to a group of formula —$NR^2R^{3a}$ in which $R^2$ is an alkyl group and $R^{3a}$ is as defined above. Finally, the ester group of this amide compound is hydrolysed to afford the desired compound of formula (VIb) wherein $R^2$ is an alkyl group and $R^3$ is a group of formula $R^{3a}$ as defined above.

The above synthetic method can be modified where it is desired to synthesise compounds of formula (VIb) wherein $R^2$ and $R^3$ together with the nitrogen atom to which they are attached form a saturated 4- to 6-membered heterocyclic ring. In this instance, the first three steps of the above synthetic method are followed to give an amide derivative having an amide group of formula —$NHR^{3a}$. This amide derivative is then reacted with an alkylating agent in which the alkyl group is substituted with a nucleophilic leaving group such as a halogen atom, followed by the addition of a base such as sodium hydride to give an intramolecular ring cyclisation reaction so as to afford a compound of formula (VIb) having the desired saturated heterocyclic ring.

The steps of Reaction Scheme A can be described in more detail as follows.

Step A

In this step a compound of formula (IV) is obtained by reaction of a compound of formula (III) with a compound of formula (VIa) or (VIb) in the presence of an organic acid such as trifluoromethanesulfonic acid or trimethylsilyl trifluorosulfonate. The organic acid, such as trifluoromethanesulfonic acid or trimethylsilyl trifluorosulfonate, acts as a catalyst, and thus the amount of acid employed does not need, in principle, to be more than a catalytic amount. However, the amount needed may vary fairly widely depending upon the reactivity of the carboxylic acid of formula (VIa) or (VIb) employed. In general, however, the amount of organic acid employed need be no more than equimolar with respect to the starting material of formula (VIa) or (VIb).

Addition of a powdery inorganic compound to the reaction mixture may, in some cases, accelerate the reaction. Examples of suitable inorganic compounds having such a property, include: metal salts, such as copper trifluoromethanesulfonate, cuprous iodide, stannic iodide, cobalt iodide or nickel iodide; Celite™; silica gel or alumina. Of these, we prefer a copper salt, such as copper trifluoromethanesulfonate or cuprous iodide, and we most prefer cuprous iodide.

Where the carboxylic acid derivative of formula (VIa) or (VIb) is only slightly soluble, a silyl ester of said corresponding carboxylic acid derivative can be used. For example, the starting compound of formula (III) can be treated with a solution of a trimethylsilyl ester of the corresponding carboxylic acid compound of formula (VIa) or (VIb) which is prepared by reaction of said carboxylic acid compound with an equivalent amount of allyltrimethylsilane in the presence of trifluoromethanesulfonic acid or trimethylsilyl trifluoromethanesulfonate as a catalyst.

The reaction is normally and preferably performed in the presence of a solvent. There is no particular restriction on the nature of the solvent used in this reaction, provide that it has no adverse effect on the reaction or on the reagents involved and that it can dissolve the reagents at least to some extent. Examples of suitable solvents include: aromatic hydrocarbons, such as benzene, toluene or xylene; and halogenated hydrocarbons such as methylene chloride, 1,2-dichloroethane or chloroform.

The reaction can take place over a wide range of temperatures, and the precise reaction temperature is not critical. The preferred reaction temperature will depend upon such factors as the nature of the solvent, and the starting materials or reagents used. However, in general we find it convenient to perform the reaction at a temperature of between −10° C. and 100° C., more preferably between 0° C. and 50° C.

The time required for the reaction may also vary widely, depending on many factors, notably the reaction temperature, and the nature of the starting materials and solvent employed. However, the reaction time is usually from 5 minutes to 6 hours, more preferably from 10 minutes to 2 hours.

Steps B1 and B2

In Step B1 or B2, the carbonyl group at the 5-position of the compound of formula (IV) produced in Step A above is reduced using a reducing agent to give a compound of formula (V) (Step B1) or (Ia) (Step B2) having a hydroxy group at the 5-position.

There is no particular limitation on the nature of the reducing agent, provided that other parts of the compound of formula (IV) are not affected by it. Examples of such reducing agents include sodium borohydride and lithium borohydride, of which we prefer sodium borohydride.

The reaction is normally and preferably performed in the presence of a solvent. There is no particular restriction on the nature of the solvent used in this reaction, provide that it has no adverse effect on the reaction or on the reagents involved and that it can dissolve the reagents at least to some extent. Examples of suitable solvents include: lower alcohols such as methanol, ethanol or propanol; and ether derivatives such as tetrahydrofuran or dimethoxyethane.

The reaction can take place over a wide range of temperatures, and the precise reaction temperature is not critical. The preferred reaction temperature will depend upon such factors as the nature of the solvent, and the starting materials or reagents used. However, in general we find it convenient to perform the reaction at a temperature of between −50° C. and 50° C.

The time required for the reaction may also vary widely, depending on many factors, notably the reaction temperature, and the nature of the starting materials and solvent employed. However, the reaction time is usually from 1 hour to 10 hours.

Step C

In Step C, a compound of formula (Ib) having an amino group at the 4-position of the phenyl group is prepared by reduction of the nitro group of the compound of formula (V) prepared in Step B1 above.

Reduction of the nitro group may be achieved in a conventional manner. For example, it may be performed by catalytic reduction using a noble metal as the catalyst. Preferred catalysts include palladium on carbon, palladium on barium sulfate and platinum oxide.

The reaction is normally and preferably performed in the presence of a solvent. There is no particular restriction on the nature of the solvent used in this reaction, provide that it has no adverse effect on the reaction or on the reagents involved and that it can dissolve the reagents at least to some extent. Examples of suitable solvents include: alcohols such as methanol or ethanol; ether derivatives such as tetrahydrofuran or dioxane; and ester derivatives such as ethyl acetate.

The reaction can take place over a wide range of temperatures, and the precise reaction temperature is not critical. The preferred reaction temperature will depend upon such factors as the nature of the solvent, and the starting materials or reagents used. However, in general we find it convenient to perform the reaction at a temperature of between 10° C. and 80° C.

The time required for the reaction may also vary widely, depending on many factors, notably the reaction temperature, and the nature of the starting materials and solvent employed. However, the reaction time is usually from 30 minutes to 5 hours.

As an alternative, reduction of the nitro group of the compound of formula (V) may be achieved using zinc powder in acetic acid. The reaction can take place over a wide range of temperatures and times, and the precise reaction temperature and time is not critical. The preferred reaction temperature and time will depend upon such factors as the nature of the solvent, and the starting materials or reagents used. However, in general we find it convenient to perform the reaction at a temperature of between 0° C. and room temperature and for a reaction time of from 30 minutes to 12 hours.

As a further alternative, reduction of the nitro group of the compound of formula (V) may be achieved using sodium borohydride in the presence of a nickel catalyst. These nickel catalysts are nickel salts such as nickel chloride or nickel bromide, preferably a triphenylphosphine complex of said nickel salts.

The reaction is normally and preferably performed in the presence of a solvent. There is no particular restriction on the nature of the solvent used in this reaction, provide that it has no adverse effect on the reaction or on the reagents involved and that it can dissolve the reagents at least to some extent. Examples of suitable solvents include: alcohols such as methanol or ethanol; and ether derivatives such as tetrahydrofuran or dioxane.

The reaction can take place over a wide range of temperatures, and the precise reaction temperature is not critical. The preferred reaction temperature will depend upon such factors as the nature of the solvent, and the starting materials or reagents used. However, in general we find it convenient to perform the reaction at a temperature of between 0° C. and room temperature.

The time required for the reaction may also vary widely, depending on many factors, notably the reaction temperature, and the nature of the starting materials and solvent employed. However, the reaction time is usually from 10 minutes to 2 hours.

Step D

In step D, a compound of formula (Ic) is prepared by reaction of a compound of formula (Ib), prepared as described in Step C above, with an acid of formula $R^{3a}OH$, wherein $R^{3a}$ is as defined above, or a reactive derivative thereof.

Reactive derivatives of compounds of formula $R^{3a}OH$ include, for example, acid halides (acid chlorides, acid bromides or the like), acid anhydrides, mixed acid anhydrides, active esters, and active amides, all of which are conventionally used in condensation reactions.

When an acid of formula $R^{3a}OH$ is used, a dehydrating agent may be used in the condensation reaction. Any dehydrating agents conventionally used in such condensation reactions may be used, and examples include dicyclohexylcarbodiimide (DCC), 2-chloro-1-methylpyridinium iodide, p-toluenesulfonic acid and sulfuric acid, of which we prefer 2-chloro-1-methylpyridinium iodide. The amount of dehydrating agent is usually from 1 to 5 molar equivalents of the acid, and is preferably from 1 to 2 molar equivalents.

The condensation reaction employing the acid of formula $R^{3a}OH$ is normally and preferably performed in the presence of a solvent. There is no particular restriction on the nature of the solvent used in this reaction, provide that it has no adverse effect on the reaction or on the reagents involved and that it can dissolve the reagents at least to some extent. Examples of suitable solvents include: hydrocarbons such as hexane, petroleum ether, benzene or toluene; halogenated hydrocarbons such as methylene chloride, 1,2-dichloroethane or chloroform; ether derivatives such as diethyl ether or tetrahydrofuran; amide derivatives such as N,N-dimethylformamide; sulfoxide derivatives such as dimethylsulfoxide; nitrile derivatives such as acetonitrile; or mixtures thereof. Preferably, the solvent employed is dichloromethane or 1,2-dichloroethane.

The reaction can take place over a wide range of temperatures, and the precise reaction temperature is not critical. The preferred reaction temperature will depend upon such factors as the nature of the solvent, and the starting materials or reagents used. However, in general we find it convenient to perform the reaction at a temperature of between −70° C. and 90° C., preferably between 0° C. and 60° C.

The time required for the reaction may also vary widely, depending on many factors, notably the reaction temperature, and the nature of the starting materials and solvent employed. However, the reaction time is usually from 15 minutes to 24 hours, preferably from 30 minutes to 6 hours.

When a reactive derivative (preferably an acid halide) of an acid having the formula $R^{3a}OH$ is used, the reaction is preferably carried out in the presence of a base. Any bases conventionally used in such condensation reactions may be used, and examples include an organic base such as triethylamine, N,N-dimethylaniline, pyridine, 4-dimethylaminopyridine, 1,5-diazabicyclo[4.3.0]non-5-ene (DBN) and 1,8-diazabicyclo[5.4.0]undec-7-ene (DBU).

The amount employed of the acid halide derivative of the acid of formula $R^{3a}OH$ is usually from 1 to 10 molar equivalents of the compound of formula (Ib) and the amount of the base employed is usually from 1 to 10 molar equivalents of the compound of formula (Ib).

The reaction is normally and preferably performed in the presence of a solvent. There is no particular restriction on the nature of the solvent used in this reaction, provide that it has no adverse effect on the reaction or on the reagents involved and that it can dissolve the reagents at least to some extent. Examples of suitable solvents include: hydrocarbons such as hexane, petroleum ether, benzene or toluene; halogenated hydrocarbons such as methylene chloride, 1,2-dichloroethane or chloroform; ether derivatives such as diethyl ether or tetrahydrofuran; amide derivatives such as N,N-dimethylformamide; sulfoxide derivatives such as dimethylsulfoxide; nitrile derivatives such as acetonitrile; or mixtures thereof. Preferably, the solvent employed is dichloromethane or 1,2-dichloroethane.

The reaction can take place over a wide range of temperatures, and the precise reaction temperature is not critical. The preferred reaction temperature will depend upon such factors as the nature of the solvent, and the starting materials or reagents used. However, in general we find it convenient to perform the reaction at a temperature of between −70° C. and 90° C., preferably between 0° C. and 50° C.

The time required for the reaction may also vary widely, depending on many factors, notably the reaction temperature and the nature of the starting materials and solvent employed. However, the reaction time is usually from 5 minutes to 24 hours, preferably from 5 minutes to 6 hours.

After completion of each of the reactions described in the Steps A to D above, the desired compound may be isolated from the reaction mixture in a conventional manner. For example, it can be obtained by neutralizing the reaction mixture as needed, removing insoluble matters by filtration, if any are present, adding organic solvents which are not miscible with each other, such as water and ethyl acetate, washing with water or the like, separating the organic layer containing the desired compound, drying it over anhydrous magnesium sulfate or the like and then distilling off the solvent.

If necessary, the desired compound thus obtained can be isolated and purified by using a conventional method such as recrystallization or reprecipitation or by a chromatographic method. Examples of chromatography include adsorption column chromatography using a carrier such as silica gel, alumina or magnesium-silica gel type Florisil, chromatography using a synthetic adsorbent, for example, partition column chromatography using a carrier such as Sephadex LH-20 (product of Pharmacia), Amberlite XAD-11 (product of Rohm & Haas) or Diaion HP-20 (product of Mitsubishi Chemical), ion exchange chromatography and normal-phase-reverse-phase column chromatography (high-performance liquid chromatography) using a silica gel or alkylated silica gel. If necessary, two or more of these techniques can be used in combination to isolate and purify the desired compound.

The starting compound of formula (III) is a natural milbemycin or a derivative thereof, these being fermentation products. The compound of formula (III) can exist as a pure single compound or a mixture having different substituents $R^1$. The compound of formula (I) can also be prepared as a pure single compound or as a mixture having different substituents $R^1$.

ILLUSTRATIVE EXAMPLES

The following examples, reference examples and test examples are intended to further illustrate the present invention and are not intended to limit the scope of the invention in any way.

Example 1

13-[1-(4-Methoxyacetylaminophenyl)cyclopentanecarbonyloxy]-5-hydroxy-milbemycin $A_4$ [(I): $R^1$=Et, $R^2$=H, $R^3$=$CH_3OCH_2CO$, a=cyclopentyl, (Compound No. 8)]

1(a) 13-[1-(4-Nitrophenyl)cyclopentanecarbonyloxy]-5-hydroxymilbemycin $A_4$ [(V): $R^1$=Et, X=$NO_2$, a=cyclopentyl]

0.18 ml trifluoromethanesulfonic acid were added to a suspension of 10.13 g (40.0 mmol) of 1-(4-nitrophenyl)cyclopentanecarboxylic acid in 150 ml of dichloromethane under a nitrogen atomosphere at room temperature. The resulting mixture was stirred for 20 minutes at the same temperature. At the end of this time, 5.57 g (10.0 mmol) of 15-hydroxy-5-oxomilbemycin $A_4$ were added and then the resulting mixture was stirred at room temperature for 30 minutes. At the end of this time, the reaction mixture was poured into 4% aqueous sodium bicarbonate solution and then extracted with ethyl acetate. The organic extract was washed successively with a 4% aqueous sodium bicarbonate solution and water, and then dried over anhydrous magnesium sulfate. The ethyl acetate was removed by distillation under reduced pressure to give crude 13-[1-(4-nitrophenyl)cyclopentanecarbonyloxy]-5-oxomilbemycin $A_4$ [(IV): $R^1$=Et, X=$NO_2$, a=cyclopentyl] which was then used in the next step without further purification.

1.52 g (40 mmol) of sodium borohydride and two drops of boron trifluoride diethyl etherate were added to a stirred solution of 13-[1-(4-nitrophenyl)cyclopentanecarbonyloxy]-5-oxomilbemycin $A_4$, prepared as described above, in 200 ml of methanol while stirring at −40° C. and the mixture was stirred for 10 minutes. At the end of this time, 400 ml of ethyl acetate were added to the reaction mixture. The ethyl acetate was washed with water three times, dried over anhydrous sodium sulfate and then removed by distillation under reduced pressure. The resulting residue was purified by chromatography on a silica gel column using a 1:1 by volume mixture of ethyl acetate and hexane as the eluant to give 6.79 g (8.75 mmol, yield 87.5%) of the title compound as an amorphous solid.

$^1$H Nuclear Magnetic Resonance Spectrum (400 MHz, $CDCl_3$) δ ppm:
8.16 (2H, doublet, J=7.9 Hz);
7.53 (2H, doublet, J=7.9 Hz);
5.70–5.90 (2H, multiplet);
5.37 (1H, singlet);
5.25–5.40 (3H, multiplet);
4.84 (1H, doublet, J=10.6 Hz);
4.67 and 4.63 (2H, AB-quartet, J=14.4 Hz);
4.28 (1H, multiplet);
4.07 (1H, singlet);
3.94 (1H, doublet, J=6.4 Hz);
3.55 (1H, multiplet);
3.25 (1H, multiplet);
3.02 (1H, multiplet);
1.88 (3H, singlet);
1.29 (3H, singlet);
0.99 (3H, triplet, J=7.3 Hz);
0.82 (3H, doublet, J=6.5 Hz);
0.77 (3H, doublet, J=6.4 Hz).

1(b) 13-[1-(4-Aminophenyl)cyclopentanecarbonyloxy]-5-hydroxymilbemycin $A_4$
[(Ib) : $R^1$=Et, a=cyclopentyl, (Compound No. 1)]

100 ml of methanol and 1.12 g (1.7 mmol) of a triphenylphosphine complex of nickel (II) chloride were added to a solution of 6.79 g (8.75 mmol) of 13-[1-(4-nitrophenyl)cyclopentanecarbonyloxy]-5-hydroxymilbemycin $A_4$, prepared as described in Example 1(a) above, in 100 ml of ethyl acetate. 1000 mg (26.5 mmol) of sodium borohydride were added in small portions to the resulting mixture over 10 minutes in an ice bath and then stirred for a further 10 minutes at the same temperature. At the end of this time, 70 ml of ethyl acetate were added to the reaction mixture and this was then washed with water three times and dried over anhydrous sodium sulfate. The ethyl acetate was removed by distillation under reduced pressure and the resulting residue was crystallized from a mixture of ethyl acetate and hexane to give 5.87 g (7.87 mmol, yield 89.9%) of the title compound as a white crystalline solid.

Melting Point: 235–239° C.

$^1$H Nuclear Magnetic Resonance Spectrum (400 MHz, CDCl$_3$) δ ppm:
7.16 (2H, doublet, J=8.6 Hz);
6.65 (2H, doublet, J=8.6 Hz);
5.77–5.84 (2H, multiplet);
5.44 (1H, singlet);
5.32–5.43 (3H, multiplet);
4.84 (1H, doublet, J=10.5 Hz);
4.70 and 4.73 (2H, AB-quartet, J=14.5 Hz);
4.33 (1H, multiplet);
4.13 (1H, singlet);
4.00 (1H, doublet, J=6.2 Hz);
3.54 (1H, multiplet);
3.30 (1H, multiplet);
3.09 (1H, multiplet);
1.92 (3H, singlet);
1.36 (3H, singlet);
1.01 (3H, triplet, J=7.3 Hz);
0.87 (3H, doublet, J=6.5 Hz);
0.82 (3H, doublet, J=6.5 Hz).

1(c) 13-[1-(4-Methoxyacetylaminophenyl) cyclopentanecarbonyloxy]-5-hydroxy-milbemycin A$_4$ [(I): R$^1$=Et, R$^2$=H, R$^3$=CH$_3$OCH$_2$CO, a=cyclopentyl, (Compound No. 8)]

0.52 g (6.4 mmol) of pyridine and 0.58 ml (6.2 mmol) of methoxyacetyl chloride were added to a solution of 4.48 g (6.0 mmol) of 13-[1-(4-aminophenyl)-cyclopentanecarbonyloxy]-5-hydroxymilbemycin A$_4$, prepared as described in Example 1(b) above, in 60 ml of tetrahydrofuran while stirring at −30° C., and the resulting mixture was then stirred for a further 10 minutes at the same temperature. At the end of this time, 250 ml of ethyl acetate were added to the reaction mixture which was then washed successively with 0.5 M citric acid solution, water, 4% aqueous sodium bicarbonate solution and water and then dried over anhydrous sodium sulfate. The ethyl acetate was then removed by distillation under reduced pressure and the resulting residue was purified by chromatography on a silica gel column using a 2:1 by volume mixture of ethyl acetate and hexane as the eluant to give 4.38 g (5.35 mmol, yield 89.2%) of the title compound as a white crystalline solid.

Melting point: 176–178° C.

$^1$H Nuclear Magnetic Resonance Spectrum (400 MHz, CDCl$_3$) δ ppm:
8.20 (1H, singlet);
7.49 (2H, doublet, J=8.6 Hz);
7.29 (2H, doublet, J=8.6 Hz);
5.77 (1H, multiplet);
5.74 (1H, multiplet);
5.39 (1H, singlet);
5.27–5.37 (3H, multiplet);
4.80 (1H, doublet, J=10.5 Hz);
4.68 and 4.64 (2H, AB-quartet, J=14.5 Hz);
4.28 (1H, multiplet);
4.08 (1H, singlet);
4.01 (2H, singlet);
3.95 (1H, doublet, J=6.4 Hz);
3.54 (1H, multiplet);
3.51 (3H, singlet);
3.25 (1H, multiplet);
3.01 (1H, multiplet);
2.64 (2H, multiplet);
2.32 (1H, doublet, J=8.1 Hz);
1.87 (3H, singlet);
0.96 (3H, triplet, J=7.3 Hz);
0.82 (3H, doublet, J=6.5 Hz);
0.76 (3H, doublet, J=6.5 Hz).
MS (FAB): 818 (M+H$^+$, M=C$_{47}$H$_{63}$NO$_{11}$).

Example 2

13-[1-(4-Acetylaminophenyl)cyclopentanecarbonyloxy]-5-hydroxymilbemycin A$_4$ [(I): R$^1$=Et, R$^2$=H, R$^3$=CH$_3$CO, a=cyclopentyl, (Compound No. 2)]

13-[1-(4-Aminophenyl)cyclopentanecarbonyloxy]-5-hydroxymilbemycin A$_4$, prepared as described in Examples 1(a) and (b) above, was treated with acetic anhydride using a similar procedure to that described in Example 1(c) above to give the title compound (yield 89.8%) as an amorphous solid.

$^1$H Nuclear Magnetic Resonance Spectrum (400 MHz, CDCl$_3$) δ ppm:
7.41 (2H, doublet, J=8.6 Hz);
7.27 (2H, doublet, J=8.6 Hz);
5.70–5.80 (2H, multiplet);
5.39 (1H, singlet);
5.25–5.40 (3H, multiplet);
4.80 (1H, doublet, J=10.6 Hz);
4.64 and 4.68 (2H, AB-quartet, J=14.2 Hz);
4.28 (1H, doublet of doublets, J=6.3 and 8.4 Hz);
4.07 (1H, singlet);
3.95 (1H, doublet, J=6.3 Hz);
3.54 (1H, multiplet);
3.25 (1H, multiplet);
3.01 (1H, multiplet);
2.61 (2H, multiplet);
2.33 (1H, doublet, J=8.4 Hz);
1.87 (3H, singlet);
1.58 (3H, singlet);
0.96 (3H, triplet, J=7.3 Hz);
0.82 (3H, doublet, J=6.5 Hz);
0.76 (3H, doublet, J=6.5 Hz).
MS (FAB): 788 (M+H$^+$, M=C$_{46}$H$_{61}$NO$_{10}$).

Example 3

13-[1-(4-Cyanoacetylaminophenyl) cyclopentanecarbonyloxy]-5-hydroxymilbemycin A$_4$ [(I): R$^1$=Et, R$^2$=H, R$^3$=NCCH$_2$CO, a=cyclopentyl, (Compound No. 6)]

13-[1-(4-Aminophenyl)cyclopentanecarbonyloxy]-5-hydroxymilbemycin A$_4$, prepared as described in Examples 1(a) and (b) above, was treated with cyanoacetyl chloride using a similar procedure to that described in Example 1(c) above to give the title compound (yield 89.8%) as an amorphous solid.

$^1$H Nuclear Magnetic Resonance Spectrum (400 MHz, CDCl$_3$) δ ppm:
7.68 (1H, singlet);
7.42 (2H, doublet, J=8.7 Hz);
7.33 (2H, doublet, J=8.7 Hz);
5.72–5.77 (2H, multiplet);
5.39 (1H, singlet);

5.28–5.37 (3H, multiplet);
4.81 (1H, doublet, J=10.6 Hz);
4.64 and 4.68 (2H, AB-quartet, J=14.5 Hz);
4.29 (1H, multiplet);
4.07 (1H, singlet);
3.95 (1H, doublet, J=6.2 Hz);
3.55 (2H, singlet);
3.52 (1H, multiplet);
3.25 (1H, multiplet);
3.01 (1H, multiplet);
2.62 (2H, multiplet);
2.32 (1H, doublet, J=8.2 Hz);
1.87 (3H, singlet);
0.96 (3H, triplet, J=7.3 Hz);
0.82 (3H, doublet, J=6.5 Hz);
0.76 (3H, doublet, J=6.5 Hz).
MS (FAB): 813 (M+H$^+$, M=$C_{47}H_{60}N_2O_{10}$).

Example 4

13-[1-(4-Methanesulfonylaminophenyl) cyclopentanecarbonyloxy]-5-hydroxy-milbemycin $A_4$ [(I): $R^1$=Et, $R^2$=H, $R^3$=$CH_3SO_2$, a=cyclopentyl, (Compound No.20)]

13-[1-(4-Aminophenyl)cyclopentanecarbonyloxy]-5-hydroxymilbemycin $A_4$, prepared as described in Examples 1(a) and (b) above, was treated with methanesulfonyl chloride using a similar procedure to that described in Example 1(c) above, to give the title compound (yield 88.2%) as an amorphous solid.

$^1$H Nuclear Magnetic Resonance Spectrum (400 MHz, CDCl$_3$) δ ppm:
7.32 (2H, doublet, J=8.7 Hz);
7.14 (2H, doublet, J=8.7 Hz);
6.47 (1H, singlet);
5.70–5.80 (2H, multiplet);
5.39 (1H, singlet);
5.25–5.37 (3H, multiplet);
4.80 (1H, doublet, J=10.6 Hz);
4.64 and 4.68 (2H, AB-quartet, J=14.0 Hz);
4.28 (1H, doublet of doublets, J=6.4 Hz, J=8.2 Hz);
4.07 (1H, singlet);
3.95 (1H, doublet, J=6.4 Hz);
3.54 (1H, multiplet);
3.25 (1H, multiplet);
3.01 (1H, multiplet);
2.93 (3H, singlet);
2.62 (2H, multiplet);
2.33 (1H, doublet, J=8.2 Hz);
1.87 (3H, singlet);
0.96 (3H, triplet, J=7.3 Hz);
0.82 (3H, doublet, J=6.5 Hz);
0.74 (3H, doublet, J=6.5 Hz).
MS (FAB): 824 (M+H$^+$, M=$C_{45}H_{61}NO_{11}S$).

Example 5

13-[1-(4-Hydroxyacetylaminophenyl) cyclopentanecarbonyloxy]-5-hydroxy-milbemycin $A_4$ [(I): $R^1$=Et, $R^2$=H, $R^3$=HOCH$_2$CO, a=cyclopentyl, (Compound No. 7)]

388 mg (0.5 mmol) of 13-[1-(4-aminophenyl) cyclopentanecarbonyloxy]-5-hydroxymilbemycin $A_4$, prepared as described in Examples 1(a) and (b) above, were treated with 114 mg (0.6 mmol) of t-butyldimethylsilyloxyacetic acid and 153 mg (0.6 mmol) of 2-chloro-1-methylpyridinium iodide using a similar procedure to that described in Example 1(c) above to afford an intermediate, 13-[1-[4-(t-butyl-dimethylsilyloxy) acetylaminophenyl]cyclopentanecarbonyloxy]-5-hydroxy-milbemycin $A_4$, which was used in the next step without further purification. 0.5 ml of a 1N solution of hydrochloric acid were added to a solution of the intermediate in 5 ml of methanol and the resulting mixture was stirred at room temperature for 5 hours. At the end of this time 25 ml of ethyl acetate were added to the reaction mixture which was then washed successively with 4% aqueous sodium bicarbonate solution and water and then dried over anhydrous sodium sulfate. The ethyl acetate was then removed by distillation under reduced pressure and the resulting residue was purified by chromatography on a silica gel column using a 3:2 by volume mixture of ethyl acetate and hexane as the eluant to give the title compound (yield 78.7%) as an amorphous solid.

1H Nuclear Magnetic Resonance Spectrum (400 MHz, CDCl$_3$) δ ppm:
8.26 (1H, singlet);
7.49 (2H, doublet, J=8.5 Hz);
7.30 (2H, doublet, J=8.5 Hz);
5.70–5.80 (2H, multiplet);
5.39 (1H, singlet);
5.25–5.40 (3H, multiplet);
4.80 (1H, doublet, J=10.4 Hz);
4.64 and 4.68 (2H, AB-quartet, J=14.4 Hz);
4.28 (1H, doublet of doublets, J=6.4 Hz, J=8.1 Hz);
4.25 (2H, doublet, J=5.2 Hz);
4.08 (1H, singlet);
3.95 (1H, doublet, J=6.4 Hz);
3.54 (1H, multiplet);
3.25 (1H, multiplet);
3.02 (1H, doublet of triplets, J=2.2 Hz, J=9.2 Hz);
2.69 (1H, triplet, J=5.2 Hz);
2.62 (2H, multiplet);
2.35 (1H, doublet, J=8.1 Hz);
1.86 (3H, singlet);
0.96 (3H, triplet, J=7.3 Hz);
0.82 (3H, doublet, J=6.5 Hz);
0.76 (3H, doublet, J=6.5 Hz).
MS (FAB): 842 (M+K, M=$C_{46}H_{61}NO_{11}$,+KI).

Example 6

13-{1-[4-(N-Acetyl-N-methylglycylamino)phenyl] cyclopentanecarbonyloxy}-5-hydroxymilbemycin $A_4$ [(I): $R^1$=Et, $R^2$=H, $R^3$=$CH_3CON(CH_3)CH_2CO$, a=cyclopentyl, (Compound No. 346)]

388 mg (0.5 mmol) of 13-[1-(4-aminophenyl) cyclopentanecarbonyloxy]-5-hydroxymilbemycin $A_4$, prepared as described in Examples 1(a) and (b) above, were treated with 79 mg (0.6 mmol) of N-acetyl-N-methylglycine and 85 mg (0.6 mmol) of 1-methyl-3-(3-dimethylaminopropyl)carbodiimide in 5 ml of tetrahydrofuran, the mixture being stirred at room temperature for 30 minutes, using a similar procedure to that described in Example 1(c) above to give the title compound (yield 87.0%) as an amorphous solid.

$^1$H Nuclear Magnetic Resonance Spectrum (400 MHz, CDCl$_3$) δ ppm:
8.51 (1H, singlet);
7.42 (2H, doublet, J=8.5 Hz);
7.26 (2H, doublet, J=8.5 Hz);
5.70–5.80 (2H, multiplet);
5.39 (1H, singlet);
5.25–5.40 (3H, multiplet);
4.80 (1H, doublet, J=10.6 Hz);
4.64 and 4.68 (2H, AB-quartet, J=14.5 Hz);
4.28 (1H, doublet of doublets, J=6.1 Hz, J=8.2 Hz);
4.09 (2H, singlet);
4.08 (1H, singlet);

3.95 (1H, doublet, J=6.1 Hz);
3.54 (1H, multiplet);
3.25 (1H, multiplet);
3.19 (3H, singlet);
3.02 (1H, doublet of triplets, J=2.3 Hz, J=9.4 Hz);
2.62 (2H, multiplet);
2.33 (1H, doublet, J=8.2 Hz);
2.18 (3H, singlet);
1.83 (3H, singlet);
0.93 (3H, triplet, J=7.2 Hz);
0.82 (3H, doublet, J=6.5 Hz);
0.76 (3H, doublet, J=6.5 Hz).
MS (FAB): 859 (M+H$^+$, M=$C_{49}H_{66}N_2O_{11}$).

Example 7
13-{1-[4-(2-Oxopyrrolidin-1-yl)acetylaminophenyl]cyclopentanecarbonyloxy}-5-hydroxymilbemycin $A_4$ [(I): $R^1$=Et, $R^2$=H, $R^3$=2-oxopyrrolidin-1-yl-$CH_2CO$, a=cyclopentyl), (Compound No. 350)]

388 mg (0.5 mmol) of 13-[1-(4-aminophenyl)cyclopentanecarbonyloxy]-5-hydroxymilbemycin $A_4$, prepared as described in Examples 1(a) and (b) above, were treated with 86 mg (0.6 mmol) of (2-oxo-pyrrolidin-1-yl) acetic acid and 85 mg (0.6 mmol) of 1-methyl-3-(3-dimethylaminopropyl)carbodiimide in 5 ml of tetrahydrofuran, the mixture being stirred at room temperature for 40 minutes, using a similar procedure to that described in Example 1(c) above to give the title compound (yield 89.5%) as an amorphous solid.

$^1$H Nuclear Magnetic Resonance Spectrum (400 MHz, $CDCl_3$) δ ppm:
8.33 (1H, singlet);
7.42 (2H, doublet, J=8.6 Hz);
7.27 (2H, doublet, J=8.6 Hz);
5.72–5.79 (2H, multiplet);
5.39 (1H, singlet);
5.28–5.37 (3H, multiplet);
4.81 (1H, doublet, J=10.6 Hz);
4.65 and 4.68 (2H, AB-quartet, J=14.4 Hz);
4.27 (1H, doublet of doublets, J=6.3 Hz, J=8.3 Hz);
4.08 (1H, singlet);
4.04 (2H, singlet);
3.95 (1H, doublet, J=6.3 Hz);
3.59 (2H, triplet, J=7.2 Hz);
3.54 (1H, multiplet);
3.25 (1H, multiplet);
3.01 (1H, multiplet);
2.60 (2H, multiplet);
2.33 (1H, doublet, J=8.3 Hz);
1.87 (3H, singlet);
0.96 (3H, triplet, J=7.3 Hz);
0.82 (3H, doublet, J=6.5 Hz);
0.76 (3H, doublet, J=6.5 Hz).
MS (FAB): 871 (M+H$^+$, M=$C_{50}H67N_2O_{11}$).

Example 8
13-[1-(4-Methoxyacetylaminophenyl)cyclopentanecarbonyloxy]-5-hydroxy-milbemycin $A_3$ [(I): $R^1$=Me, $R^2$=H, $R^3$=$CH_3OCH_2CO$, a=cyclopentyl, (Compound No. 51)]

8(a) 13-[1-(4-Aminophenyl)cyclopentanecarbonyloxy]-5-hydroxymilbemycin $A_3$
[(I): $R^1$=Me, $R^2$=H, $R^3$=H, a=cyclopentyl, (Compound No. 44)]

Similar procedures were adopted to those described in Examples 1(a) and (b) above, but using 15-hydroxy-5-oxomilbemycin $A_3$ as a starting material instead of 15-hydroxy-5-oxomilbemycin $A_4$, to afford the title compound (yield 67.5%) as an amorphous solid which was used in the next step without further purification.

$^1$H Nuclear Magnetic Resonance Spectrum (400 MHz, $CDCl_3$) δ ppm:
7.11 (2H, doublet, J=8.5 Hz);
6.60 (2H, doublet, J=8.5 Hz);
5.71–5.78 (2H, multiplet);
5.38 (1H, singlet);
5.25–5.40 (3H, multiplet);
4.80 (1H, doublet, J=10.6 Hz);
4.65 and 4.68 (2H, AB-quartet, J=13.9 Hz);
4.28 (1H, multiplet);
4.08 (1H, singlet);
3.95 (1H, doublet, J=6.1 Hz);
3.59 (2H, broad singlet);
3.52 (1H, multiplet);
3.18–3.26 (2H, multiplet);
2.57 (2H, multiplet);
1.87 (3H, singlet);
1.31 (3H, singlet);
1.13 (3H, doublet, J=6.4 Hz);
0.83 (3H, doublet, J=6.5 Hz);
0.77 (3H, doublet, J=6.6 Hz).

(b) 13-[1-(4-Methoxyacetylaminophenyl)cyclopentanecarbonyloxy]-5-hydroxy-milbemycin $A_3$ [(I): $R^1$=Me, $R^2$=H, $R^3$=$CH_3OCH_2CO$, a=cyclopentyl, (Compound No. 51)]

13-[1-(4-Aminophenyl)cyclopentanecarbonyloxy]-5-hydroxymilbemycin $A_3$, prepared as described in Example 8(a) above, was treated with methoxyacetyl chloride using a similar procedure to that described in Example 1(c) above, to give the title compound, which was recrystallised from methanol and water to give the purified title compound (yield 92.3%) as a white crystalline solid.

Melting point: 239–242° C.

$^1$H Nuclear Magnetic Resonance Spectrum (400 MHz, $CDCl_3$) δ ppm:
8.21 (1H, singlet);
7.49 (2H, doublet, J=8.6 Hz);
7.29 (2H, doublet, J=8.6 Hz);
5.71–5.78 (2H, multiplet);
5.38 (1H, singlet);
5.24–5.36 (3H, multiplet);
4.80 (1H, doublet, J=10.6 Hz);
4.64 and 4.68 (2H, AB-quartet, J=13.7 Hz);
4.28 (1H, multiplet);
4.07 (1H, singlet);
4.01 (2H, singlet);
3.95 (1H, doublet, J=6.3 Hz);
3.51 (3H, singlet);
3.50 (1H, multiplet);
3.18–3.26 (2H, multiplet);
2.61 (2H, multiplet);
1.87 (3H, singlet);
1.28 (3H, singlet);
1.13 (3H, doublet, J=6.3 Hz);
0.83 (3H, doublet, J=6.6 Hz);
0.76 (3H, doublet, J=6.5 Hz).
MS (FAB): 804 (M+H$^+$, M=$C_{46}H_{61}NO_{11}$).

Example 9
13-[1-(4-Methanesulfonylaminophenyl)cyclopentanecarbonyloxy]-5-hydroxy-milbemycin $A_3$ [(I): $R^1$=Me, $R^2$=H, $R^3$=$CH_3SO_2$, a=cyclopentyl), (Compound No. 63)]

13-[1-(4-Aminophenyl)cyclopentanecarbonyloxy]-5-hydroxymilbemycin $A_3$, prepared as described in Example 8(a) above, was treated with methanesulfonyl chloride using a similar procedure to that described in Example 1(c) above, to give the title compound (yield 88.9%) as an amorphous solid.

$^1$H Nuclear Magnetic Resonance Spectrum (400 MHz, CDCl$_3$) δ ppm:
7.33 (2H, doublet, J=8.6 Hz);
7.14 (2H, doublet, J=8.6 Hz);
6.40 (1H, singlet);
5.73–5.80 (2H, multiplet);
5.38 (1H, singlet);
5.25–5.40 (3H, multiplet);
4.80 (1H, doublet, J=10.6 Hz);
4.64 and 4.68 (2H, AB-quartet, J=14.4 Hz);
4.28 (1H, doublet of doublets, J=6.4 Hz, J=8.4 Hz);
4.07 (1H, singlet);
3.95 (1H, doublet, J=6.4 Hz);
3.51 (1H, multiplet);
3.17–3.25 (2H, multiplet);
2.97 (3H, singlet);
2.63 (2H, multiplet);
2.32 (1H, doublet, J=8.4 Hz);
1.87 (3H, singlet);
1.29 (3H, singlet);
1.13 (3H, doublet, J=6.1 Hz);
0.82 (3H, doublet, J=6.5 Hz);
0.74 (3H, doublet, J=6.6 Hz).
MS (FAB): 810 (M+H$^+$, M=C$_{44}$H$_{59}$NO$_{11}$S).

Example 10

13-Deoxy-13β-[1-(4-methoxyacetylaminophenyl) cyclopentanecarbonyloxy]-22,23-dihydroavermectin B$_{1a}$ aglycone
[(I): R$^1$=s-Bu, R$^2$=H, R$^3$=CH$_3$OCH$_2$CO, a=cyclopentyl, (Compound No. 137)]

(a) 13-Deoxy-13β-[1-(4-aminophenyl) cyclopentanecarbonyloxy]-22,23-dihydroavermectin B$_{1a}$ aglycone
[(I): R$^1$=s-Bu, R$^2$=H, R$^3$=H, a=cyclopentyl, (Compound No. 130)]

Adopting similar procedures to those described in Examples 1(a) and (b) above, but using 13-epi-5-oxo-22, 23-dihydroavermectin B$_{1a}$ instead of 15-hydroxy-5-oxomilbemycin A$_4$, the title compound was obtained which was purified by chromatography on a silica gel column using a 3:2 by volume mixture of ethyl acetate and hexane as the eluant to give the purified title compound (yield 48.5%) as an amorphous solid.

$^1$H Nuclear Magnetic Resonance Spectrum (400 MHz, CDCl$_3$) δ ppm:
7.11 (2H, doublet, J=8.6 Hz);
6.60 (2H, doublet, J=8.6 Hz);
5.72–5.80 (2H, multiplet);
5.41 (1H, singlet);
5.23–5.36 (3H, multiplet);
4.80 (1H, doublet, J=10.4 Hz);
4.65 and 4.68 (2H, AB-quartet, J=14.4 Hz);
4.28 (1H, doublet of doublets, J=6.4 Hz, J=8.1 Hz);
4.01 (1H, singlet);
3.95 (1H, doublet, J=6.4 Hz);
3.59 (2H, broad singlet);
3.56 (1H, multiplet);
3.14 (1H, multiplet);
2.58 (2H, multiplet);
2.33 (1H, doublet, J=8.1 Hz);
1.87 (3H, singlet);
1.31 (3H, singlet);
0.93 (3H, triplet, J=7.4 Hz);
0.84 (3H, doublet, J=6.7 Hz);
0.78 (3H, doublet, J=5.4 Hz);
0.77 (3H, doublet, J=6.6 Hz).

(b) 13-Deoxy-13β-[1-(4-methoxyacetylaminophenyl) cyclopentanecarbonyloxy]-22,23-dihydroavermectin B$_{1a}$ aglycone
[(I): R$^1$=s-Bu, R$^2$=H, R$^3$=CH$_3$OCH$_2$CO, a=cyclopentyl]

13-Deoxy-13β-[1-(4-aminophenyl) cyclopentanecarbonyloxy]-22,23-dihydroavermectin B$_{1a}$ aglycone, prepared as described in Example 10(a) above, was treated with methoxyacetyl chloride using a similar procedure to that described in Example 1(c) above to give the title compound (yield 86.0%) as an amorphous solid.

$^1$H Nuclear Magnetic Resonance Spectrum (400 MHz, CDCl$_3$) δ ppm:
8.21 (1H, singlet);
7.49 (2H, doublet, J=8.7 Hz);
7.30 (2H, doublet, J=8.7 Hz);
5.72–5.80 (2H, multiplet);
5.41 (1H, singlet);
5.22–5.35 (3H, multiplet);
4.81 (1H, doublet, J=10.4 Hz);
4.65 and 4.68 (2H, AB-quartet, J=14.4 Hz);
4.29 (1H, doublet of doublets, J=6.3 Hz, J=8.3 Hz);
4.01 (2H, singlet);
4.00 (1H, singlet);
3.95 (1H, doublet, J=6.3 Hz);
3.56 (1H, multiplet);
3.51 (3H, singlet);
3.25 (1H, multiplet);
3.13–3.24 (1H, multiplet);
2.62 (2H, multiplet);
2.32 (1H, doublet, J=8.3 Hz);
1.87 (3H, singlet);
1.28 (3H, singlet);
0.94 (3H, triplet, J=7.4 Hz);
0.84 (3H, doublet, J=6.9 Hz);
0.78 (3H, doublet, J=5.6 Hz);
0.76 (3H, doublet, J=6.6 Hz).
MS (FAB): 846 (M+H$^+$, M=C$_{49}$H$_{67}$NO$_{11}$).

Example 11

13-Deoxy-13β-[1-(4-methanesulfonylaminophenyl) cyclopentanecarbonyloxy]-22,23-dihydroavermectin B$_{1a}$ aglycone
[(I): R$^1$=s-Bu, R$^2$=H, R$^3$=CH$_3$SO$_2$, a=cyclopentyl, (Compound No. 149)]

13-Deoxy-13β-[1-(4-aminophenyl) cyclopentanecarbonyloxy]-22,23-dihydroavermectin B$_{1a}$ aglycone, prepared as described in Example 10(a) above, was treated with methanesulfonyl chloride using a similar procedure to that described in Example 1(c) above to give the title compound (yield 87.4%) as an amorphous solid.

$^1$H Nuclear Magnetic Resonance Spectrum (400 MHz, CDCl$_3$) δ ppm:
7.33 (2H, doublet, J=8.5 Hz);
7.14 (2H, doublet, J=8.5 Hz);
6.36 (1H, singlet);
5.73–5.80 (2H, multiplet);
5.40 (1H, singlet);
5.22–5.36 (3H, multiplet);
4.81 (1H, doublet, J=10.4 Hz);
4.64 and 4.67 (2H, AB-quartet, J=14.5 Hz);
4.29 (1H, doublet of doublets, J=6.3 Hz, J=8.1 Hz);
4.01 (1H, singlet);
3.95 (1H, doublet, J=6.3 Hz);
3.56 (1H, multiplet);
3.26 (1H, multiplet);
3.14 (1H, multiplet);

2.97 (3H, singlet);
2.63 (2H, multiplet);
2.32 (1H, doublet, J=8.1 Hz);
1.86 (3H, singlet);
1.29 (3H, singlet);
0.93 (3H, triplet, J=7.3 Hz);
0.84 (3H, doublet, J=7.0 Hz);
0.78 (3H, doublet, J=5.6 Hz);
0.75 (3H, doublet, J=6.5 Hz).
MS (FAB): 852 (M+H$^+$, M=C$_{47}$H$_{65}$NO$_{11}$S).

Example 12

13-{1-[4-(N-Methoxyacetyl-N-methylamino)phenyl] cyclopentanecarbonyloxy}-5-hydroxymilbemycin A$_4$ [(I): R$^1$=Et, R$^2$=Me, R$^3$=CH$_3$OCH$_2$CO, a=cyclopentyl, (Compound No. 35)]

A similar procedure to that described in Example 1(a) above was employed, but using 1-[4-(N-Methoxyacetyl-N-methylamino)phenyl]cyclopetanecarboxylic acid instead of 1-(4-nitrophenyl)cyclopentanecarboxylic acid to afford the title compound (yield 48.0%) as an amorphous solid.

$^1$H Nuclear Magnetic Resonance Spectrum (400 MHz, CDCl$_3$) δ ppm:
7.40 (2H, doublet, J=8.6 Hz);
7.12 (2H, doublet, J=8.6 Hz);
5.70–5.80 (2H, multiplet);
5.39 (1H, singlet);
5.25–5.40 (3H, multiplet);
4.81 (1H, doublet, J=10.5 Hz);
4.68 and 4.64 (2H, AB-quartet, J=14.5 Hz);
4.28 (1H, multiplet);
4.08 (1H, singlet);
3.94 (1H, doublet, J=6.3 Hz);
3.67 (2H, singlet);
3.54 (1H, multiplet);
3.33 (3H, singlet);
3.25 (1H, multiplet);
3.24 (3H, singlet);
3.01 (1H, multiplet);
2.64 (2H, multiplet);
1.87 (3H, singlet);
0.96 (3H, triplet, J=7.3 Hz);
0.82 (3H, doublet, J=6.5 Hz);
0.76 (3H, doublet, J=6.5 Hz).
MS (FAB): 832 (M+H$^+$, M=C$_{48}$H$_{65}$NO$_{11}$).

Example 13

13-{1-[4-(2-Oxazolidon-3-yl)phenyl] cyclopentanecarbonyloxy}-5-hydroxy-milbemycin A$_4$ [(I): R$^1$=Et, R$^2$,R$^3$=2-oxazolidon-3-yl, a=cyclopentyl, (Compound No. 42)]

A similar procedure to that described in Example 1(a) was employed, but using 1-[4-(2-oxazolidon-3-yl)phenyl] cyclopetanecarboxylic acid instead of 1-(4-nitrophenyl) cyclopentanecarboxylic acid, to afford the title compound (yield 34.2%) as an amorphous solid.

$^1$H Nuclear Magnetic Resonance Spectrum (400 MHz, CDCl$_3$) δ ppm:
7.46 (2H, doublet, J=8.7 Hz);
7.34 (2H, doublet, J=8.7 Hz);
5.70–5.80 (2H, multiplet);
5.39 (1H, singlet);
5.25–5.40 (3H, multiplet);
4.81 (1H, doublet, J=10.4 Hz);
4.68 and 4.64 (2H, AB-quartet, J=14.6 Hz);
4.49 (2H, multiplet);
4.28 (1H, doublet of doublets, J=6.1 Hz, J=8.3 Hz);
4.08 (2H, multiplet);
4.07 (1H, singlet);
3.95 (1H, doublet, J=6.1 Hz);
3.54 (1H, multiplet);
3.25 (1H, multiplet);
3.01 (1H, multiplet);
2.61 (2H, multiplet);
2.33 (1H, doublet, J=8.3 Hz);
1.87 (3H, singlet);
0.96 (3H, triplet, J=7.3 Hz);
0.82 (3H, doublet, J=6.3 Hz);
0.76 (3H, doublet, J=6.5 Hz).
MS (FAB): 815 (M+H$^+$, M=C$_{47}$H$_{61}$NO$_{11}$).

Example 14

13-[1-(4-Methoxyacetylaminophenyl) cyclopentanecarbonyloxy]-5-hydroxy-milbemycin A$_4$ [(I): R$^1$=Et, R$^2$=H, R$^3$=CH$_3$OCH$_2$CO, a=cyclopentyl, (Compound No. 8)]

14(a) 13-[1-4-Methoxyacetylaminophenyl) cyclopentanecarbonyloxy]-5-oxomilbemycin A$_4$ [(IV): R$^1$=Et, X=CH$_3$OCH$_2$CONH, a=cyclopentyl]

3.16 ml (20.0 mmol) of allyltrimethylsilane and 0.6 ml of trimethylsilyl trifluoromethanesulfonate were added at room temperature to a suspension of 8.28 g (30 mmol) of 1-(4-methoxyacetylaminophenyl)cyclopentanecarboxylic acid (prepared as described in Reference Example 1 below) in 120 ml of dichloromethane and the resulting mixture was stirred at room temperature under a nitrogen atomosphere for 20 minutes. At the end of this time, 5.57 g (10.0 mmol) of 15-hydroxy-5-oxomilbemycin A$_4$ were added at room temperature to the resulting clear mixture and this mixture was stirred for 60 minutes at the same temperature. At the end of this time, the reaction mixture was partitioned between a 4% aqueous sodium bicarbonate solution and ethyl acetate. The ethyl acetate layer was washed successively with a 4% aqueous sodium bicarbonate solution and water, dried over anhydrous magnesium sulfate and then the ethyl acetate was removed by distillation under reduced pressure to afford the title compound, which was used in the next reaction step without further purification.

14(b) 13-[1-(4-Methoxyacetylaminophenyl) cyclopentanecarbonyloxy]-5-hydroxymilbemycin A$_4$ 1.52 g (40 mmol) of sodium borohydride and 2 drops of boron trifluoride diethyl etherate were added at −40° C. to a solution of the 5-oxo derivative prepared in Example 14(a) above in 200 ml of methanol and the resulting mixture was stirred at the same temperature for 10 minutes. After the reaction was completed, 400 ml of ethyl acetate were added to the reaction mixture, and the ethyl acetate layer was washed three times with water, dried over anhydrous sodium sulfate and then the ethyl acetate was removed by distillation under reduced pressure. The resulting residue was purified by chromatography on a silica gel column using a 1:1 by volume mixture of ethyl acetate and hexane as the eluant to give 5.32 g (yield 65%) of the title compound. This was recrystallized from a mixture of isopropanol and water to afford crystals having a melting point of 176–178° C. The physicochemical properties of this product, such as the $^1$H Nuclear Magnetic Resonance Spectrum, were identical to those of the compound obtained in Example 1 above.

Anal. Cal. for C$_{47}$H$_{63}$NO$_{11}$.H$_2$O: C: 67.53%, H: 7.84%, N: 1.68%
Found: C: 67.80%, H: 7.49%, N: 1.75%

Examples 15 to 19

The compound prepared in Example 20 below was treated with the reagents mention in Examples 15 to 19 below using a similar procedure to that described in Example 1(c) above, to afford the title compounds of Examples 15 to 19 below.

Example 15
13-[1-(4-Methoxyacetylaminophenyl)cyclobutanecarbonyloxy]-5-hydroxy-milbemycin $A_4$ [(I): $R^1$=Et, $R^2$=H, $R^3$=$CH_3OCH_2CO$, a=cyclobutyl, (Compound No. 180)]
Reagent: methoxyacetyl chloride
Yield: 74.3%
$^1$H Nuclear Magnetic Resonance Spectrum (400 MHz, $CDCl_3$) δ ppm:
8.23 (1H, singlet);
7.52 (2H, doublet, J=8.6 Hz);
7.24 (2H, doublet, J=8.6 Hz);
5.75 and 5.79 (2H, multiplet);
5.39 (1H, singlet);
5.29~5.36 (3H, multiplet);
4.84 (1H, doublet, J=10.5 Hz);
4.65 and 4.68 (2H, AB-quartet, J=13.7 Hz);
4.28 (1H, multiplet);
4.06 (1H, singlet);
4.02 (2H, singlet);
3.95 (1H, doublet, J=6.1 Hz);
3.55 (1H, multiplet);
3.51 (3H, singlet);
3.25 (1H, multiplet);
3.02 (1H, multiplet);
1.87 (3H, singlet);
1.33 (3H, singlet);
0.97 (3H, triplet, J=7.3 Hz);
0.82 (3H, doublet, J=6.5 Hz);
0.76 (3H, doublet, J=6.5 Hz).
MS (FAB): 804 (M+H$^+$, M=$C_{46}H_{61}NO_{11}$).

Example 16
13-[1-(4-Acetylaminophenyl)cyclobutanecarbonyloxy]-5-hydroxymilbemycin $A_4$
[(I): $R^1$=Et, $R^2$=H, $R^3$=$CH_3CO$, a=cyclobutyl, (Compound No. 174)]
Reagent: acetic anhydride
Yield: 83.2%
$^1$H Nuclear Magnetic Resonance Spectrum (400 MHz, $CDCl_3$) δ ppm:
7.44 (2H, doublet, J=8.3 Hz);
7.22 (2H, doublet, J=8.3 Hz);
7.14 (1H, singlet);
5.75~5.78 (2H, multiplet);
5.39 (1H, singlet);
5.29~5.37 (3H, multiplet);
4.84 (1H, doublet, J=10.5 Hz);
4.65 and 4.68 (2H, AB-quartet, J=14.0 Hz);
4.28 (1H, multiplet);
4.06 (1H, singlet);
3.95 (1H, doublet, J=6.3 Hz);
3.54 (1H, multiplet);
3.25 (1H, multiplet);
3.02 (1H, multiplet);
2.18 (3H, singlet);
1.87 (3H, singlet);
1.33 (3H, singlet);
0.97 (3H, triplet, J=7.3 Hz);
0.82 (3H, doublet, J=6.5 Hz);
0.76 (3H, doublet, J=6.5 Hz).
MS (FAB): 774 (M+H$^+$, M=$C_{45}H_{59}NO_{10}$).

Example 17
13-[1-(4-Methanesulfonylaminophenyl)cyclobutanecarbonyloxy]-5-hydroxy-milbemycin $A_4$ [(I): $R^1$=Et, $R^2$=H, $R^3$=$CH_3SO_2$, a=cyclobutyl, (Compound No. 192)]
Reagent: methanesulfonyl chloride
Yield: 70.5%
$^1$H Nuclear Magnetic Resonance Spectrum (400 MHz, $CDCl_3$) δ ppm:
7.27 (2H, doublet, J=8.6 Hz);
7.17 (2H, doublet, J=8.6 Hz);
6.43 (1H, singlet);
5.76~5.78 (2H, multiplet);
5.39 (1H, singlet);
5.28~5.37 (3H, multiplet);
4.84 (1H, doublet, J=10.6 Hz);
4.65 and 4.69 (2H, AB-quartet, J=13.4 Hz);
4.29 (1H, multiplet);
4.06 (1H, singlet);
3.95 (1H, doublet, J=6.4 Hz);
3.55 (1H, multiplet);
3.25 (1H, multiplet);
3.02 (1H, multiplet);
2.98 (3H, singlet);
1.87 (3H, singlet);
1.33 (3H, singlet);
0.97 (3H, triplet, J=7.3 Hz);
0.82 (3H, doublet, J=6.5 Hz);
0.76 (3H, doublet, J=6.5 Hz).
MS (FAB): 810 (M+H$^+$, M=$C_{44}H_{59}NO_{11}S$).

Example 18
13-[1-(4-Trifluoroacetylaminophenyl)cyclobutanecarbonyloxy]-5-hydroxy-milbemycin $A_4$ [(I): $R^1$=Et, $R^2$=H, $R^3$=$CF_3CO$, a=cyclobutyl, (Compound No. 175)]
Reagent : trifluoroacetic anhydride
Yield: 70.7%
$^1$H Nuclear Magnetic Resonance Spectrum (400 MHz, $CDCl_3$) δ ppm:
7.85 (1H, singlet);
7.52 (2H, doublet, J=8.5 Hz);
7.30 (2H, doublet, J=8.5 Hz);
5.76~5.79 (2H, multiplet);
5.39 (1H, singlet);
5.27~5.37 (3H, multiplet);
4.85 (1H, doublet, J=10.4 Hz);
4.65 and 4.68 (2H, AB-quartet, J=13.7 Hz);
4.28 (1H, multiplet);
4.06 (1H, singlet);
3.95 (1H, doublet, J=6.2 Hz);
3.54 (1H, multiplet);
3.25 (1H, multiplet);
3.01 (1H, multiplet);
1.87 (3H, singlet);
1.33 (3H, singlet);
0.97 (3H, triplet, J=7.3 Hz);
0.82 (3H, doublet, J=6.5 Hz);
0.77 (3H, doublet, J=6.5 Hz).
MS (FAB): 828 (M+H$^+$, M=$C_{45}H_{56}F_3NO_{10}$).

Example 19
13-[1-(4-Pentynoylaminophenyl)cyclobutanecarbonyloxy]-5-hydroxymilbemycin $A_4$
[(I): $R^1$=Et, $R^2$=H, $R^3$=$CH{\equiv}CCH_2CH_2CO$, a=cyclobutyl (Compound No. 354)]
Reagent: 4-pentynoic acid/2-chloro-1-methylpyridinium iodide
Yield: 37.9%
$^1$H Nuclear Magnetic Resonance Spectrum (400 MHz, $CDCl_3$) δ ppm:
7.46 (2H, doublet, J=8.5 Hz);
7.34 (1H, singlet);
7.23 (2H, doublet, J=8.5 Hz);
5.72~5.79 (2H, multiplet);
5.39 (1H, singlet);
5.29~5.37 (3H, multiplet);

4.84 (1H, doublet, J=10.4 Hz);
4.65 and 4.68 (2H, AB-quartet, J=13.5 Hz);
4.28 (1H, multiplet);
4.05 (1H, singlet);
3.95 (1H, doublet, J=6.1 Hz);
3.55 (1H, multiplet);
3.25 (1H, multiplet);
3.02 (1H, multiplet);
2.56~2.66 (4H, multiplet);
1.87 (3H, singlet);
1.34 (3H, singlet);
0.97 (3H, triplet, J=7.3 Hz);
0.82 (3H, doublet, J=6.5 Hz);
0.77 (3H, doublet, J=6.5 Hz).
MS (FAB): 812 (M+H$^+$, M=$C_{48}H_{61}NO_{10}$).

Example 20

13-[1-(4-Aminophenyl)cyclobutanecarbonyloxy]-5-hydroxymilbemycin $A_4$

[(I): $R^1$=Et, $R^2$=H, $R^3$=H, a=cyclobutyl, (Compound No. 173)]

Similar procedures to those described in Examples 1(a), (b) and (c) were adopted, but using 1-(4-nitrophenyl)cyclobutanecarboxylic acid instead of 1-(4-nitrophenyl)cyclopentanecarboxylic acid, to afford the title compound as an amorphous solid in a yield of 59.8%.

$^1$H Nuclear Magnetic Resonance Spectrum (400 MHz, CDCl$_3$) δ ppm:

7.10 (2H, doublet, J=8.5 Hz);
6.74 (2H, doublet, J=8.5 Hz);
5.75 and 5.79 (2H, multiplet);
5.39 (1H, singlet);
5.29~5.38 (3H, multiplet);
4.84 (1H, doublet, J=10.4Hz);
4.68 and 4.65 (2H, AB-quartet, J=14.5 Hz);
4.28 (1H, multiplet);
4.06 (1H, singlet);
3.95 (1H, doublet, J=6.4 Hz);
3.55 (1H, multiplet);
3.25 (1H, multiplet);
3.02 (1H, multiplet);
1.87 (3H, singlet);
1.35 (3H, singlet);
0.97 (3H, triplet, J=7.3 Hz);
0.82 (3H, doublet, J=6.5 Hz);
0.78 (3H, doublet, J=6.5 Hz).
MS (FAB): 732 (M+H$^+$, M=$C_{43}H_{57}NO_9$).

Example 21

8:2 mixture of 13-[1-(4-methoxyacetylaminophenyl)cyclopentanecarbonyloxy]-5-hydroxymilbemycin $A_4$ and 13-[1-(4-methoxyacetylaminophenyl)cyclopentanecarbonyloxy]-5-hydroxymilbemycin $A_3$ [(I): $R^1$=Et:Me (8:2), $R^2$=H, $R^3$=$CH_3OCH_2CO$ a=cyclopentyl, (Compound Nos. 8 and 51)]

A 8:2 (by mass) mixture of 13-[1-(4-methoxyacetylaminophenyl)cyclpentane-carbonyloxy]-5-hydroxymilbemycin $A_4$ and 13-[1-(4-methoxyacetylaminophenyl)-cyclopentanecarbonyloxy]-5-hydroxymilbemycin $A_3$ was obtained using essentially the same procedure described in Example 1 above, but using as a starting material an 8:2 (by mass) mixture of 15-hydroxy-5-oxomilbemycin $A_4$ and 15-hydroxy-5-oxomilbemycin $A_3$ instead of 15-hydroxy-5-oxomilbemycin $A_4$.

Reference Example 1

1-(4-Methoxyacetylaminophenyl)cyclopentanecarboxylic acid 13 g (20 mmol) of triphenylphosphine complex of nickel (II) chloride were added to a solution of 25.3 g (100 mmol) of 1-(4-nitrophenyl)cyclopentanoic acid in 200 ml of a 1:1 by volume mixture of methanol and tetrahydrofuran cooled in an ice bath. 10 g of sodium boronhydride were added to the cooled mixture in small portions over 10 minutes. The resulting mixture was then stirred at room temperature for 20 minutes, at the end of which time the reaction mixture was poured into 500 ml of water and the pH was then adjusted to 4 with concentrated hydrochloric acid. This caused the precipitation of crystals of 1-(4-aminophenyl)cyclopentanecarboxylic acid which were collected by filtration. 22.2 g (150 mmol) of potassium carbonate and 100 ml of tetrahydrofuran were then added to a suspension of the crystalline product in 100 ml of water which had been cooled in an ice bath, after which 9.0 ml (100 mmol) of methoxyacetyl chloride were added. After stirring the resulting mixture at the same temperature for 30 minutes, 200 ml of water were added, the mixture was washed with ether and the pH of the ether extract was then adjusted to 4 with concentrated hydrochloric acid. This mixture was allowed to stand at room temperature for 2 hours and the resulting crystals were collected by filtration to afford 25.4 g (yield 91.6%) of the desired compound as white crystals.

Mp 162–163° C.

$^1$H Nuclear Magnetic Resonance Spectrum (400 MHz, CDCl$_3$) δ ppm:

8.24(1H, singlet);
7.50 (2H, doublet, J=8.7 Hz);
7.35 (2H, doublet, J=8.7 Hz);
4.00 (1H, singlet);
3.49 (3H, singlet);
2.63 (2H, multiplet);
1.90 (2H, multiplet);
1.73 (4H, multiplet).

Test Example 1

Test on Insecticidal Effect Against Cat Fleas

A test container wherein the living space of fleas was isolated from bovine serum by use of Parafilm™ (obtainable from Aldrich Chemical Co. Ltd.), which is usually used as an artificial skin, was prepared. A compound to be tested was added to the bovine serum in an amount sufficient for its concentration to be 1 ppm, and the fleas were allowed to suck the serum sample through the Parafilm™ at 37° C. Each group consisted of 20 fleas. From the number of fleas which had died after 48 hours, the insecticidal effect of the test compound against fleas was evaluated. By counting the dead fleas in a control group without a test compound, the mortality was corrected. The results are shown in Table 2.

TABLE 2

| Compound | Mortality (%) |
| --- | --- |
| Example 1(b) | 95.0 |
| Example 1(c) | 90.2 |
| Example 2 | 95.0 |
| Example 3 | 81.4 |
| Example 4 | 100.0 |
| Example 5 | 74.4 |
| Example 6 | 79.5 |
| Example 8 | 87.6 |
| Example 9 | 83.2 |
| Milbemycin $A_4$ | 20.9 |
| Comparative Compound A | 2.4 |

It should be noted that Compound A in the above table is a compound which is disclosed in EP-A-0246739 and is represented by the following formula:

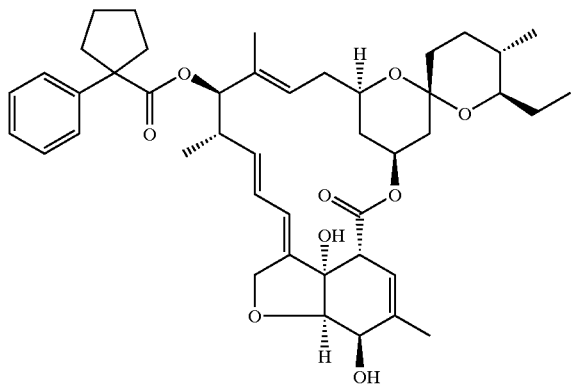

Compound A

Test Example 2
Test on Elimination of Fleas From Dogs

Beagles provided for the test were infected with cat fleas prior to the commencement of the test. The number of fleas collected from the surface of the body of the dog three days after infection was counted and an infection ratio, calculated as the ratio of the fleas counted three days after infection to the initial number used to infect the dog, was determined for each dog.

The test compound 13-[1-(4-methoxyacetylaminophenyl) cyclopentane-carbonyloxy]-5-hydroxymilbemycin $A_4$, prepared as described in Example 1(c) above, was dissolved in a 9:1 by volume mixture of benzyl alcohol and propylene carbonate to give a test solution in which the test compound is present at a concentration of 10% (w/v). The resulting test solution was administered dropwise to the interscapular region of each of four test beagles (4 to 7 months old) at a dose of 5 mg/kg body weight. On Day 7, Day 21 and Day 28 after administration of the test compound, each dog was infected with 100 cat fleas. The number of fleas collected from the surface of the bodies of the dogs three days after infection was counted. The number of fleas obtained before and after administration was determined to give an elimination ratio.

In the tests, no fleas were collected from the surfaces of the bodies of the dogs three days after infection with the fleas on each of Day 7, Day 21 and Day 28. Thus, even 28 days after administration of the test compound, the elimination ratio was 100%.

In a control, four dogs which had not had the test compound administered were studied. No significant variation in the infection ratios was observed over the period of the tests when the infection tests were conducted for this control group at the same time as for the test group.

Test Example 3
Test on Elimination of Fleas from Dogs

The procedure of Test Example 2 above was repeated using as the test solution a 10% (w/v) solution of the 8:2 mixture of 13-[1-(4-methoxyacetylaminophenyl)-cyclopentanecarbonyloxy]-5-hydroxymilbemycin $A_4$ and 13-[1-(4-methoxyacetyl-aminophenyl) cyclopentanecarbonyloxy]-5-hydroxymilbemycin $A_3$, prepared as described in Example 21 above, in a 9:1 by volume mixture of benzyl alcohol and propylene carbonate. In the tests, no fleas were collected from the surfaces of the bodies of the test dogs three days after infection with the fleas on each of Day 7, Day 21 and Day 28. Thus, even 28 days after administration of the test compound, the elimination ratio was 100%.

Test Examples 4, 5 and 6

Test example 4: Test on effect against roundworms (*Toxocara canis*)
Test example 5: Test on effect against hookworms (*Ancylostoma caninum*)
Test example 6: Test on effect against whipworms (*Trichuris vulpis*)

13-[1-(4-Methoxyacetylaminophenyl) cyclopentanecarbonyloxy]-5-hydroxymilbemycin $A_4$, prepared as described in Example 1(c) above, was dissolved in a 9:1 by volume mixture of benzyl alcohol and propylene carbonate to give a 10% (w/v) test solution which was administered dropwise at a dose of 5 mg/kg body weight to the poll region of each of the test dogs naturally infected with either roundworm, hookworm or whipworm (i.e. dogs were kept in surroundings where the parasites existed and dogs which became infected were chosen for the tests). For each of these three parasites, the number of eggs per gram (EPG) of dog faeces excreted was measured before, and 7 to 9 days after, administration of the test compound. The number of worms excreted in the faeces of the dog (WEF) between administration of the test compound and the end of the test was measured. Upon completion of the test, each of the test dogs was subjected to post mortem to count the number of surviving worms in the digestive tract (SWDT). The results are shown in Table 3.

TABLE 3

| Dog No. | EPG Before Administration | EPG after 7–9 Days | WEF | SWDT | Elimination ratio (%) |
|---|---|---|---|---|---|
| Test 4 (roundworm elimination test) | | | | | |
| 1 | 6,800 | 0 | 3 | 0 | 100 |
| 2 | 2,400 | 0 | 5 | 0 | 100 |
| 3 | 40,400 | 0 | 8 | 0 | 100 |
| Test 5 (hookworm elimination test) | | | | | |
| 4 | 200 | 0 | — | 0 | 100 |
| 5 | 3,000 | 0 | — | 0 | 100 |
| 6 | 200 | 0 | — | 0 | 100 |
| Test 6 (whipworm elimination test) | | | | | |
| 7 | 34 | 0 | — | 0 | 100 |
| 8 | 5 | 0 | — | 0 | 100 |

As can be seen from the above, the test compound showed excellent activity in eliminating roundworms from the test dogs. Before dropwise administration of the test compound, the EPG level was very high. However, the EPG level was reduced to 0 by 7 to 9 days after administration of the test compound. The post mortem study of the digestive tracts of the test dogs found that there were no surviving worms.

The effectiveness of the test compound was also evident in the tests studying elimination of hookworms and whipworms from the test dogs. 7 to 9 days after administration, the EPG level was reduced to 0 and no surviving hookworms or whipworms were found in the digestive tract.

As can be understood from the above results, the test compound showed excellent anthelmintic activity against the tested parasitic worms in the digestive tract.

Test Example 7
Test on Effect against Perforating Scabies (*Sarcoptes scabiei*)

Dogs and cats naturally infected with scabies were provided for the test. A 10% (w/v) test solution of 13-[1-(4-methoxyacetylaminophenyl)cyclopentane-carbonyloxy]-5-hydroxymilbemycin $A_4$, prepared as described in Example 1(c), in a 9:1 by volume mixture of benzyl alcohol and propylene carbonate was prepared. This was administered at a rate of 5 mg/kg body weight to a test animal in its poll region. The epidermis was scraped off the test animal from its ears and limbs before administration and then three weeks after administration of the test compound. The epidermis thus obtained was then charged in a 10% potassium hydroxide solution and the number of worm bodies and eggs was observed microscopically. The results are shown in Table 4.

TABLE 4

| Animals to be tested | Before administration | | After administration (three weeks later) | |
|---|---|---|---|---|
| | Worm body | Egg | Worm body | Egg |
| Dog | 70 | 11 | 9 | 0 |
| Cat | 35 | 86 | 0 | 0 |

The results above show that clear effects against scabies were confirmed when test compound was administered dropwise in the poll region of each of the dogs and cats in which infection with scabies had been confirmed. The number of scabies remaining in the tested dogs after three weeks was only 9 and their oviposition was prevented completely. In the cat, on the other hand, 100% effects and 100% oviposition preventing effects were observed. Thus, the results demonstrate clearly that the test compound has an excellent effect against scabies.

Test Example 8
Test on Activity Against Microfilariae

From a dog infected with *Dirofilaria immitis*, microfilariae (mf) were collected. The inhibitory effect of 13-[1-(4-methoxyacetylaminophenyl)-cyclopentanecarbonyloxy]-5-hydroxymilbemycin $A_4$, prepared as described in Example 1(c) above, against mf was studied by culturing mf, 13-[1-(4-methoxy-acetylaminophenyl)cyclopentanecarbonyloxy]-5-hydroxymilbemycin $A_4$ (100 ng/ml) and neutrophils. The mf were obtained by subjecting the blood obtained from the infected dog to hemolysis with saponin. Neutrophils were obtained by intraperitoneally injecting casein into a rat to induce its transmigration, followed by density gradient centrifugation. Broths containing mf alone, mf plus neutrophils, mf plus test compound and mf plus test compound plus neutrophils were prepared, and these were then cultured at 37° C. in a 5% $CO_2$ incubator. The percentage reduction of mf when compared to the mf present at the end of the test in the broth containing mf only, were measured for the broths containing neutrophils, the test compound and the test compound plus neutrophils. The results are shown in Table 5.

TABLE 5

| Conditions | Percentage reduction of microfilariae |
|---|---|
| mf + neutrophils | 6.0 |
| mf + test compound | 0.02 |
| mf + neutrophils + test compound | 53.8 |

Activity against mf (the pre-larval stage of nematodes) acts as a model for testing the activity of a test compound against infection with *Dirofilaria immitis*. As a result of the study on the test compound in the present test system, it can be seen that the test compound has good activity against mf in the presence of neutrophils. From these results, it can be deduced that the test compound will have a preventive effect against infection with *Dirofilaria immitis*.

Test Example 9
Test on Miticidal Effect Against Two-Spotted Spider Mites

A cowpea leaf having the mites parasite thereon was dipped for about 10 seconds in a solution containing 100 ppm of 13-[1-(4-methoxyacetylaminophenyl)-cyclopentanecarbonyloxy]-5-hydroxymilbemycin $A_4$, prepared as described in Example 1(c) above, said solution being prepared by taking a solution containing 10000 ppm of said compound in a 95:5 by volume mixture of acetone and water and then diluting it with water. The remainder of the test compound solution was removed and the treated leaf was allowed to stand in a Petri dish containing a sponge covered with a filter paper soaked in water. After the test compound solution on the leaf had dried, eggs of the mites were marked. The leaf was then allowed to stand at 25° C. on the Petri dish without a lid. Two days after treatment with the test compound, the death rate of mites (expressed as a percentage of the total number of mites) was determined. Seven to ten days after the treatment, the "death rate" of the mite eggs (expressed as the percentage of the total number of mite eggs which were unhatched) and the death rate of the hatchlings (expressed as the percentage of the total number of hatchlings which were killed) was estimated. The test was repeated at different concentrations of the test compound. "Untreated" in this test means the control test in which water was used instead of the test compound solution. The results are shown in Tables 6 and 7.

TABLE 6

| Compound | Concentration (ppm) | two-spotted spider mite (2 days after) | | | | The death rate of mites (%) |
|---|---|---|---|---|---|---|
| | | total | dead | agony | escape | |
| Test Compound Solution | 100 | 48 | 48 | — | — | 100 |
| | 10 | 39 | 39 | — | — | 100 |
| | 1 | 55 | 55 | — | — | 100 |
| | 0.1 | 65 | 64 | 1 | — | 98.5 |
| untreated | — | 37 | 0 | | | 0 |

TABLE 7

| Compound | Concentration (ppm) | The egg of two-spotted spider mite (7 days after) | | Death rate of mite eggs (%) | Death rate of hatchlings (%) |
|---|---|---|---|---|---|
| | | Total | dead | | |
| Test Compound Solution | 100 | 20 | 18 | 90 | 100 |
| | 10 | 20 | 5 | 25 | 100 |
| | 1 | 20 | 0 | 0 | 30 |
| untreated | — | 20 | 0 | 0 | 0 |

From these results, it can be seen that the test compound has miticidal activity, including activity against adult mites, eggs and hatchlings.

Test Example 10
Test on Insecticidal Effect Against Southern Root-Knot Nematode

An agar plate (80 ml: containing 1.25 ppm of kanamycin, 1.25 ppm of streptomycin and 0.8585 ppm of penicillin) was prepared in a container (70×70×20 mm). The plate was planted with a cucumber in the cotyledon stage of development. Filter paper disks (thin ones having a diameter of 8 mm) were dipped in a solution containing 1000 ppm of 13-[1-(4-methoxyacetylaminophenyl)cyclopentane-carbonyloxy]-5-hydroxymilbemycin $A_4$, prepared as described in Example 1(c) above, in a 95:5 by volume mixture of acetone and water. One of the thus-treated paper disks was put into the agar plate and two further treated paper disks were laid over the cotyledon.

After treatment, the container was covered with an acrylic plate to prevent water evaporation. Four days later, about 2.5 ml of a suspension containing 500 second-stage larvae of Southern root-knot nematode were added dropwise to the agar plate. Ten days after addition of the larvae, the number of galls of nematodes was estimated. Each test was conducted at a temperature of 25° C. and a humidity of 65%. "Untreated" in this test is a control in which water was used to soak the filter paper instead of the test compound solution. The following criteria were used to judge the results obtained:

0: equal to the treatment-free group (51 to 150 galls)
1: slightly less than the treatment-free group (36 to 50 galls)
2: less than the treatment-free group (21 to 35 galls)
3: markedly less than the treatment-free group (0 to 20 galls)

The results are shown in Table 8.

TABLE 8

| Compound | Concentration (ppm) | Number of galls | Effect (result) |
|---|---|---|---|
| Test compound | 1000 | 6 | 3 |
| Untreated | — | 115 | 0 |

From these results, it can be seen that the test compound is effective in eliminating Southern root-knot nematode.

Test Example 11
Test on the Insecticidal Effect Against Termites

A test filter paper was treated with 20 μg of an acetone solution containing a 8:2 mixture of 13-[1-(4-methoxyacetylaminophenyl)cyclopentanecarbonyloxy]-5-hydroxymilbemycin $A_4$ and 13-[1-(4-methoxyacetylaminophenyl)cyclopentane-carbonyloxy]-5-hydroxymilbemycin $A_3$, prepared as described in Example 21, at a predetermined concentration and then dried in the air. A sample tube was charged with the test filter paper and 10 worker termites, and then put in a dark place at a temperature of 26±1° C. Four days after treatment, the death rate of the termites was determined. The "Control" is a filter paper which was treated with acetone in the absence of a test compound and then dried in the air. The results are shown in Table 9.

TABLE 9

| | Death rate (%) | | | |
|---|---|---|---|---|
| | 500 ppm | 250 ppm | 125 ppm | 62.5 ppm |
| Test compound | 100 | 100 | 100 | 100 |
| Control | | | | 0 |

From these results, it can be concluded that test compound is effective in eliminating termites.

Test Example 12
Test on Insecticidal Effect Against Cat Fleas

A test container wherein the living space of fleas was isolated from bovine serum by use of Parafilm™ (obtainable from Aldrich Chemical Co. Ltd.), which is usually used as an artificial skin, was prepared. A compound to be tested was added to the bovine serum in an amount sufficient for its concentration to be 1 ppm, and the fleas were allowed to suck the serum sample through the Parafilm™ at 37° C. Each group consisted of 20 fleas. From the number of fleas which had died after 48 hours, the insecticidal effect of the test compound against fleas was evaluated. By counting the dead fleas in a control group without a test compound, the mortality was corrected. The results are shown in Table 10.

TABLE 10

| Compound | Mortality (%) |
|---|---|
| Example 15 | 100 |
| Example 16 | 92.9 |
| Example 17 | 94.9 |
| Example 18 | 91.5 |
| Example 19 | 90.7 |
| Milbemycin $A_4$ | 20.9 |
| Compound A | 2.4 |

Compound A is the same compound described in Test example 1.

The milbemycin derivatives of formula (I) and agriculturally, horticulturally, pharmaceutically and veterinarily acceptable salts thereof according to the present invention have excellent insecticidal, anthelmintic and acaricidal activity and further have excellent prophylactic activity against various diseases caused by insects and other parasites which are parasitic on animals, including humans. Their insecticidal effects are particularly good against fleas parasitic on domestic animals or humans [for example, cat fleas (Ctenocephalides felis) and dog fleas (Ctenocephalides canis)]. The milbemycin derivatives of formula (I) and salts thereof according to the present invention are also useful as agrochemicals, as insecticides for use against harmful wood-eating insects and as sanitary insecticides which are used to protect public health, e.g., insecticides to eliminate cockroaches or flies.

The milbemycin derivatives of formula (I) and veterinarily acceptable salts thereof according to the present invention thereof have, in the field of veterinary medicines, excellent insecticidal activity, for example, against insects harmful to animals [e.g. Gasterophilidae, Hypodermatidae, Oestridae, Muscidae, Cuterbridae, Haematopinidae, Linognathidae, Pediculidae, Menoponidae, Philopteridae, Trichodectidae, Cimicidae or Reduviidae] and also show good activity against various other harmful parasites to animals such as worms [e.g. exo-parasites such as Ixodidae, Halarachnidae, Dermanyssidae, Argasidae, Demodicidae, Psoroptidae, Sarcoptidae].

The milbemycin derivatives of formula (I) and agriculturally and horticulturally acceptable salts thereof according to the present are also highly effective in controlling various diseases caused by horticultural pests. In particular, the compounds of the present invention have excellent acaricidal activity not only against adults or eggs of spider mites such as Tetranychidae, Eriophyidae and the like but also against acarids which have acquired resistance to existing acaricides and which have therefore posed a serious problem in recent years. They also have excellent acaricidal activity against Meloidogyne, Bursapholenchus, Phizoglyphus and the like found in the soil and in the trunk or bark of trees.

The milbemycin derivatives of formula (I) and agriculturally and horticulturally acceptable salts thereof according to the present invention have excellent insecticidal activity and are therefore useful as an insecticide. The compounds of the present invention exhibit strong preventive effects against harmful insects but show no phytotoxicity, so that agricultural plants can be treated effectively without causing them any damage. The milbemycin derivatives of formula (I) and agriculturally and horticulturally acceptable salts thereof according to the present invention are also of use in the elimination of a variety of pests, including noxious insects which damage plants by sucking or biting them, other plant parasites, noxious insects which are harmful to stored products, harmful wood-eating insects and insects for sanitary reasons. Examples of such pests include coleoptera such as *Callosobruchus chinensis, Sitophilus zeamais, Tribolium castaneum, Epilachna vigitioctomaculata, Agriores fuscicollis, Anomala rufocuprea, Leptinotarsa decemkineata,* Diabrotica spp., *Monochamus alternatus, Lissorhoptrus oryzophilus* and Lyctusbruneus; lepidoptera such as *Lymantria dispar, Malacosoma neustria, Pieris rapae, Spodptera litura, Mamestra brassicae, Chilosuppressalis, Pyrausta nubilalis, Ephestia cautella, Adoxophyes orana, Carpocapsa pomonella, Agrotis fucosa, Galleria mellonella* and *Plutella mylostella*; hemiptera such as *Nephotettix cincticeps, Nilaparvata lugens, Pseudococcus comstocki, Unaspis yanonensis, Myzus persicae, Aphis pomi, Aphis gossypii, Rhopalosiphum pseudobrassicas, Stephanitis nashi,* Nazara spp., *Cimex lectularius, Trialeurodes vaporariorum* and Psylla spp.; orthoptera such as *Blatella germanica, Periplaneta americana, Periplaneta fuliginosa, Gryllotalpa africana* and *Locusta migratoria migratoriodes*; isoptera such as *Deucotermes speratus* and *Coptotermes formosamus*: and diptera such as *Musca domestica, Aedes aegypti, Hylemia platura, Culex pipiens, Anopheles sinensis, Fannia canicularis* and *Culex tritaeniorhynchus*.

The milbemycin derivatives of formula (I) and pharmaceutically and veterinarily acceptable salts thereof according to the present invention have excellent parasiticidal activity and are useful anthelmintic agents against parasites in animals and humans. In particular, they exhibit excellent parasiticidal activity against nematodes [e.g. nematodes belonging to Haemonchus, Trichostrongylus, Ostertagia, Nematodirus, Cooperia, Ascaris, Bunostomum, Oesophagostomum, Chabertia, Trichuris, Metastrongylus, Strongylus, Trichonema, Dictyocaulus, Capillaria, Heterakis, Toxocara, Ascaridia, Strongyliodes, Protostrongylus, Thelazia, Habronema, Spirocerca, Physocephalus, Gongylonema, Gnathostoma, Physaloptera, Oxyuris, Ancylostoma, Uncinaria, Toxascaris and Parascaris] which are parasites in domestic animals, poultry and animals of agricultural importance such as swine, sheep, goats, cattle, horses, dogs, cats or fowls The compounds of the present invention are highly effective against certain parasites belonging to Nematodirus, Cooperia or Oesophagostomum, which attack the intestinal tract, those belonging to Haemonchus or Ostertagia found in the stomach and those belonging to Dictyocaulus found in the lungs. They also exhibit excellent parasiticidal activity against parasites belonging to Filariidae and Setariidae which are found in other tissues or organs such as the heart, blood vessels and subcutaneous and lymphatic tissues.

The compounds of the present invention are also effective against parasites found in humans and therefore exhibit excellent parasiticidal activity against parasites which are commonly observed in the digestive tracts of humans such as those belonging to Ancylostoma, Necator, Asdaris, Strongyloides, Trichinella, Capillaria, Trichuris or Enterobius.

The compounds of the present invention even exhibit excellent parasiticidal activity against parasites which can be observed in the blood, or in tissues and organs outside the digestive tract and which can be medically important, for example parasites belonging to Parafilaria, Wuchereria, Brugia, Litomosoides, Onchocerca, Elaeophara, Dirofilaria, or Loa spp. of Filariidae, Neurofilaria, Setaria, Dipetalonema, Stephanofilaria, Neurofilaria of Setariidae and Aproctidae, those belonging to Dracunculus spp. of Dracunculidae and those belonging to Strongyloides or Trichinella spp. which are intestinal parasites which can exist exceptionally under parenteral parasitic conditions.

A parasiticidal or insecticidal effective amount of a compound of the present invention (or salt thereof as described herein) is administered to a host (or site) in need of such treatment. Said compounds or salts thereof may also be administered or applied to prevent infestation, e.g., to protect the plant or animal or a non-animate site from attack by parasites or insects.

When the milbemycin derivatives of formula (1) and pharmaceutically and veterinarily acceptable salts thereof according to the present invention are used as anthelmintic agent in animals, whether human or non-human, they can be administered orally in a unit dosage form, for example as a liquid drink or as a dried solid, or in the form of a dispersion in animal feedstuffs; parenterally in the form of an injection of the compound dissolved or dispersed in a liquid carrier excipient; or topically in the form of a topical application of the compound dissolved in a solvent.

The liquid drinks may comprise a solution, suspension or dispersion of the active compound in an appropriate carrier, e.g., non-toxic solvent or water, usually in admixture with a suspending agent such as bentonite, a wetting agent or other excipients, and further optionally in admixture with an anti-foaming agent. The liquid drink formulations typically contain the active ingredient in an amount of from about 0.01 to 0.5 wt. % by weight, preferably from 0.01 to 0.1 wt. %.

For oral administration in a unit dosage form as a dried solid, capsules, pills or tablets containing the desired amount of the active ingredient can be employed. These compositions can be prepared by uniformly mixing the active ingredient with suitable pulverized carrier, e.g., diluents, fillers, disintegrators and/or binding agents (e.g. starch, lactose, talc, magnesium stearate, vegetable rubber and the like). The weight and contents of the preparation can be changed as necessary depending upon the nature of the animal to be treated, the severity of infection, the nature of the parasite, and the body weight of the animal to be treated.

When the compound of the present invention is administered as an additive (usually admixed with a liquid or non-liquid carrier) to animal feedstuffs, it can be used as a uniform dispersion in the feed, as a top dressing or in the form of pellets. Desirable antiparasitic effects can be obtained by incorporation of the compound of the present invention in the feedstuff in an amount of from 0.0001 to 0.02% by weight.

The milbemycin derivatives of formula (I) and veterinarily acceptable salts thereof according to the present invention, when dissolved or dispersed in a liquid carrier excipient, can be administered parenterally to animals by proventricular, intramuscular, intrabronchial or subcutaneous injection. For parenteral administration, the compound of the invention is preferably mixed with a vegetable oil such as peanut oil or cotton seed oil. Desirable anthelmintic effects are generally obtainable by incorporating the compound of the invention in an amount of from 0.05 to 50 wt. % by weight of the injectable formulation.

When an active ingredient of the present invention is dissolved in a solvent carrier for administration directly to a desired topical site, a solvent which is known to heighten percutaneous absorptivity can be used. Examples include alcohol derivatives such as ethanol, isopropanol, oleyl alcohol and benzyl alcohol; carboxylic acid derivatives such as lauric acid and oleic acid; ester derivatives such as isopropyl myristate and propylene carbonate; sulfoxide derivatives such as dimethylsulfoxide; or amide derivatives such as N-methylpyrrolidone; or mixtures of the above-exemplified solvents.

The amount of the milbemycin derivative of formula (I) or the pharmaceutically or veterinarily acceptable salt thereof according to the present invention to be used for attaining the best results when treating parasitical infections in animals will differ depending upon the nature of the animal to be treated, and the nature and severity of said infection. For oral administration, satisfactory results are achieved when the dose is from about 0.01 to 100 mg, preferably from 0.5 to 50.0 mg per 1 kg of the body weight of the animal, e.g., human. The compound can typically be administered in from one to six portions per day over a period of from 1 to 5 days. However, the precise nature of the administration must take into taking account the precise condition of the animal, e.g., human, to be treated.

The present invention provides methods for applying an insecticidal effective amount of the active compound or salt thereof to wood or soil to protect the wood or soil from attack by wood-eating (wood-harmful) insects. Formulations of emulsion type or microcapsule type contain the active compounds or salt thereof in amounts of from 0.01 $g/m^2$ to 5 $g/m^2$, preferably from 0.1 $g/m^2$ to 2 $g/m^2$ of wood or soil surface.

The present invention also provides methods for applying a parasiticidal effective amount of the active compound or salt thereof to plants or horticultural sites to protect against parasitic insects or nematodas by spraying liquid or dust formulations containing an effective amount of active compound or salt thereof from 0.001 wt. % to 1 wt. %, preferaly from 0.1 wt. % to 0.5 wt. % of plant surface or sites described hereinbefore.

What is claimed is:

1. A compound of formula (I) or an agriculturally, horticulturally, pharmaceutically or veterinarily acceptable salt thereof:

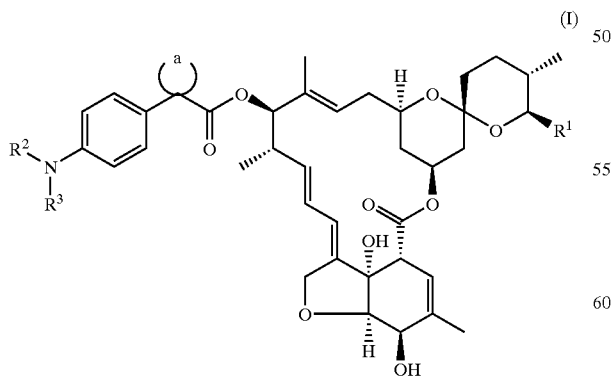

wherein:
$R^1$ represents a methyl group, ethyl group, isopropyl group or s-butyl group;

$R^2$ represents a hydrogen atom or an alkyl group having from 1 to 6 carbon atoms;

$R^3$ represents a hydrogen atom, an alkanoyl group having from 1 to 6 carbon atoms which may optionally be substituted with 1, 2 or 3 substitutents selected independently from Substituents A defined below, an alkenoyl group having from 3 to 5 carbon atoms which may optionally be substituted with 1 or 2 substitutents selected independently from Substituents A defined below, an alkynoyl group having from 3 to 5 carbon atoms which may optionally be substituted with 1 or 2 substitutents selected independently from Substituents A defined below, an alkylsulfonyl group in which the alkyl moiety has from 1 to 6 carbon, or an alkoxycarbonyl group in which the alkoxy moiety has from 1 to 6 carbon atoms, or $R^2$ and $R^3$ together with the nitrogen atom to which they are attached form a saturated 4- to 6-membered heterocyclic ring group containing one ring nitrogen atom and optionally containing one further ring heteroatom selected from the group consisting of sulfur atoms, oxygen atoms and nitrogen atoms, said saturated heterocyclic ring optionally being substituted with 1 or 2 substituents independently selected from Substituents B defined below;

the moiety -a- together with the carbon atom to which it is attached forms a 3- to 6-membered cycloalkyl group;

Substituents A are selected from the group consisting of halogen atoms, cyano groups, hydroxy groups, alkoxy groups having from 1 to 6 carbon atoms, alkylthio groups having from 1 to 6 carbon atoms, alkanoyloxy groups having from 1 to 6 carbon atoms, amino groups which may optionally be substituted with 1 or 2 substituents selected from the group consisting of alkyl groups having from 1 to 6 carbon atoms atoms, alkanoyl groups having from 1 to 6 carbon atoms, alkylsulfonyl groups in which the alkyl moiety has from 1 to 6 carbon and alkoxycarbonyl groups in which the alkoxy moiety has from 1 to 6 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with 1 or 2 substituents independently selected from Substituents B defined below;

Substituents B are selected from the group consisting of halogen atoms, cyano groups, hydroxy groups, alkoxy groups having from 1 to 6 carbon atoms, alkylthio groups having from 1 to 6 carbon atoms, alkanoyloxy groups having from 1 to 6 carbon atoms, amino groups which may optionally be substituted with 1 or 2 substituents selected from the group consisting of alkyl groups having from 1 to 6 carbon atoms atoms, alkanoyl groups having from 1 to 6 carbon atoms, alkylsulfonyl groups in which the alkyl moiety has from 1 to 6 carbon and alkoxycarbonyl groups in which the alkoxy moiety has from 1 to 6 carbon atoms and oxo groups.

2. A compound of formula (I) or an agriculturally, horticulturally, pharmaceutically or veterinarily acceptable salt thereof according to claim 1, wherein $R^1$ represents a methyl group or an ethyl group.

3. A compound of formula (I) or an agriculturally, horticulturally, pharmaceutically or veterinarily acceptable salt thereof according to claim 1, wherein $R^2$ represents a hydrogen atom or an alkyl group having from 1 to 3 carbon atoms.

4. A compound of formula (I) or an agriculturally, horticulturally, pharmaceutically or veterinarily acceptable salt thereof according to claim 2, wherein $R^2$ represents a hydrogen atom or a methyl group.

5. A compound of formula (I) or an agriculturally, horticulturally, pharmaceutically or veterinarily acceptable salt thereof according to claim 2, wherein $R^2$ represents a hydrogen atom.

6. A compound of formula (I) or an agriculturally, horticulturally, pharmaceutically or veterinarily acceptable salt thereof according to claim 1, wherein $R^3$ represents:

a hydrogen atom, an alkanoyl group having from 1 to 4 carbon atoms which may optionally be substituted with 1, 2 or 3 substituents independently selected from the group consisting of halogen atoms, cyano groups, hydroxy groups, alkoxy groups having from 1 to 3 carbon atoms, alkylthio groups having from 1 to 3 carbon atoms, alkanoyloxy groups having from 1 to 4 carbon atoms, amino groups which may optionally be substituted with 1 or 2 substituents selected from the group consisting of alkyl groups having from 1 to 3 carbon atoms, alkanoyl groups having from 1 to 4 carbon atoms, alkylsulfonyl groups in which the alkyl moiety has from 1 to 3 carbons and alkoxycarbonyl groups in which the alkoxy moiety has from 1 to 4 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with an oxo group, an alkynoyl group having from 3 to 5 carbon atoms, an alkylsulfonyl group in which the alkyl moiety has from 1 to 3 carbon atoms, or an alkoxycarbonyl group in which the alkoxy group has from 2 to 5 carbon atoms.

7. A compound of formula (I) or an agriculturally, horticulturally, pharmaceutically or veterinarily acceptable salt thereof according to claim 3, wherein $R^3$ represents a hydrogen atom or an acetyl group which is optionally substituted with a substituent selected from the group consisting of halogen atoms, cyano groups, hydroxy groups, alkoxy groups having from 1 to 3 carbon atoms, alkylthio groups having from 1 to 3 carbon atoms, alkanoyloxy groups having from 1 to 4 carbon atoms, amino groups, amino groups substituted with 1 or 2 substituents selected from the group consisting of alkyl groups having from 1 to 3 carbon atoms atoms, alkanoyl groups having from 1 to 4 carbon atoms, alkylsulfonyl groups in which the alkyl moiety has from 1 to 3 carbons and alkoxycarbonyl groups in which the alkoxy moiety has from 1 to 4 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with an oxo group.

8. A compound of formula (I) or an agriculturally, horticulturally, pharmaceutically or veterinarily acceptable salt thereof according to claim 4, wherein $R^3$ represents a hydrogen atom, an acetyl group, a hydroxyacetyl group, a methoxyacetyl group, an ethoxyacetyl group or a trifluoroacetyl group.

9. A compound of formula (I) or an agriculturally, horticulturally, pharmaceutically or veterinarily acceptable salt thereof according to claim 5, wherein $R^3$ represents a methoxyacetyl group.

10. A compound of formula (I) or an agriculturally, horticulturally, pharmaceutically or veterinarily acceptable salt thereof according to claim 1, wherein $R^2$ and $R^3$ together with the nitrogen atom to which they are attached form a saturated 4- to 6-membered heterocyclic ring group containing one ring nitrogen atom and optionally containing one further ring heteroatom selected from the group consisting of sulfur atoms, oxygen atoms and nitrogen atoms, said saturated heterocyclic ring optionally being substituted with an oxo group.

11. A compound of formula (I) or an agriculturally, horticulturally, pharmaceutically or veterinarily acceptable salt thereof according to claim 1, wherein $R^2$ and $R^3$ together with the nitrogen atom to which they are attached form a 2-pyrrolidinon-1-yl group or 2-oxazolidinon-3-yl group.

12. A compound of formula (I) or an agriculturally, horticulturally, pharmaceutically or veterinarily acceptable salt thereof according to claim 2, wherein $R^2$ and $R^3$ together with the nitrogen atom to which they are attached form a 2-oxazolidinon-3-yl group.

13. A compound of formula (I) or an agriculturally, horticulturally, pharmaceutically or veterinarily acceptable salt thereof according to claim 1, wherein the moiety -a- together with the carbon atom to which it is attached form a cyclobutyl group or a cyclopentyl group.

14. A compound of formula (I) or an agriculturally, horticulturally, pharmaceutically or veterinarily acceptable salt thereof according to claim 8, wherein the moiety -a- together with the carbon atom to which it is attached form a cyclopentyl group.

15. A compound of formula (I) or an agriculturally, horticulturally, pharmaceutically or veterinarily acceptable salt thereof according to claim 1 wherein:

$R^1$ represents a methyl group, ethyl group, isopropyl group or s-butyl group;

$R^2$ represents a hydrogen atom or an alkyl group having from 1 to 3 carbon atoms;

$R^3$ represents a hydrogen atom, an alkanoyl group having from 1 to 4 carbon atoms which may optionally be substituted with 1, 2 or 3 substituents independently selected from the group consisting of halogen atoms, cyano groups, hydroxy groups, alkoxy groups having from 1 to 3 carbon atoms, alkylthio groups having from 1 to 3 carbon atoms, alkanoyloxy groups having from 1 to 4 carbon atoms, amino groups which may optionally be substituted with 1 or 2 substituents selected from the group consisting of alkyl groups having from 1 to 3 carbon atoms, alkanoyl groups having from 1 to 4 carbon atoms, alkylsulfonyl groups in which the alkyl moiety has from 1 to 3 carbons and alkoxycarbonyl groups in which the alkoxy moiety has from 1 to 4 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with an oxo group, an alkynoyl group having from 3 to 5 carbon atoms, an alkylsulfonyl group in which the alkyl moiety has from 1 to 3 carbon atoms, or an alkoxycarbonyl group in which the alkoxy group has from 2 to 5 carbon atoms, or R² and R³ together with the nitrogen atom to which they are attached form a saturated 4- to 6-membered heterocyclic ring group containing one ring nitrogen atom and optionally containing one further ring heteroatom selected from the group consisting of sulfur atoms, oxygen atoms and nitrogen atoms, said saturated heterocyclic ring optionally being substituted with an oxo group; and the moiety -a- together with the carbon atom to which it is attached form a cyclobutyl group or a cyclopentyl group.

16. A compound of formula (I) or an agriculturally, horticulturally, pharmaceutically or veterinarily acceptable salt thereof according to claim 1 wherein:

R¹ represents a methyl group, ethyl group, isopropyl group or s-butyl group;

R² represents a hydrogen atom or an alkyl group having from 1 to 3 carbon atoms;

R³ represents a hydrogen atom, an alkanoyl group having from 1 to 4 carbon atoms which may optionally be substituted with 1 or 2 substituents independently selected from the group consisting of halogen atoms, cyano groups, hydroxy groups, alkoxy groups having from 1 to 3 carbon atoms, alkylthio groups having from 1 to 3 carbon atoms, alkanoyloxy groups having from 1 to 4 carbon atoms, amino groups which may optionally be substituted with 1 or 2 substituents selected from the group consisting of alkyl groups having from 1 to 3 carbon atoms, alkanoyl groups having from 1 to 4 carbon atoms, alkylsulfonyl groups in which the alkyl moiety has from 1 to 3 carbons and alkoxycarbonyl groups in which the alkoxy moiety has from 1 to 4 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with an oxo group, an alkynoyl group having from 3 to 5 carbon atoms, an alkylsulfonyl group in which the alkyl moiety has from 1 to 3 carbon atoms, or an alkoxycarbonyl group in which the alkoxy group has from 2 to 5 carbon atoms, or R² and R³ together with the nitrogen atom to which they are attached form a saturated 4- to 6-membered heterocyclic ring group containing one ring nitrogen atom and optionally containing one further ring heteroatom selected from the group consisting of sulfur atoms, oxygen atoms and nitrogen atoms, said saturated heterocyclic ring optionally being substituted with an oxo group; and the moiety -a- together with the carbon atom to which it is attached form a cyclobutyl group or a cyclopentyl group;

with the proviso that R² and R³ cannot both represent a hydrogen atom.

17. A compound of formula (I) or an agriculturally, horticulturally, pharmaceutically or veterinarily acceptable salt thereof according to claim 1 wherein:

R¹ represents a methyl group or an ethyl group;

R² and R³ together with the nitrogen atom to which they are attached form a saturated 4- to 6-membered heterocyclic ring group containing one ring nitrogen atom and optionally containing one further ring heteroatom selected from the group consisting of sulfur atoms, oxygen atoms and nitrogen atoms, said saturated heterocyclic ring optionally being substituted with an oxo group; and the moiety -a- together with the carbon atom to which it is attached form a cyclobutyl group or a cyclopentyl group.

18. A compound of formula (I) or an agriculturally, horticulturally, pharmaceutically or veterinarily acceptable salt thereof according to claim 1 wherein:

R¹ represents a methyl group or an ethyl group;

R² and R³ together with the nitrogen atom to which they are attached form a 2-pyrrolidinon-1-yl group or 2-oxazolidinon-3-yl group; and the moiety -a- together with the carbon atom to which it is attached form a cyclopentyl group.

19. A compound of formula (I) or an agriculturally, horticulturally, pharmaceutically or veterinarily acceptable salt thereof according to claim 1 wherein:

R¹ represents a methyl group or an ethyl group;

R² and R³ together with the nitrogen atom to which they are attached form a 2-oxazolidinon-3-yl group; and the moiety -a- together with the carbon atom to which it is attached form a cyclopentyl group.

20. A compound of formula (I) or an agriculturally, horticulturally, pharmaceutically or veterinarily acceptable salt thereof according to claim 1 wherein:

R¹ represents a methyl group or an ethyl group;

R² represents a hydrogen atom or an alkyl group having from 1 to 3 carbon atoms;

R³ represents a hydrogen atom, an alkanoyl group having from 1 to 4 carbon atoms which may optionally be substituted with 1 or 2 substituents independently selected from the group consisting of halogen atoms, cyano groups, hydroxy groups, alkoxy groups having from 1 to 3 carbon atoms, alkylthio groups having from 1 to 3 carbon atoms, alkanoyloxy groups having from 1 to 4 carbon atoms, amino groups which may optionally be substituted with 1 or 2 substituents selected from the group consisting of alkyl groups having from 1 to 3 carbon atoms, alkanoyl groups having from 1 to 4 carbon atoms, alkylsulfonyl groups in which the alkyl moiety has from 1 to 3 carbons and alkoxycarbonyl groups in which the alkoxy moiety has from 1 to 4 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with an oxo group, an alkynoyl group having from 3 to 5 carbon atoms, an alkylsulfonyl group in which the alkyl moiety has from 1 to 3 carbon atoms, or an alkoxycarbonyl group in which the alkoxy group has from 2 to 5 carbon atoms; and the moiety -a- together with the carbon atom to which it is attached form a cyclobutyl group or a cyclopentyl group.

21. A compound of formula (I) or an agriculturally, horticulturally, pharmaceutically or veterinarily acceptable salt thereof according to claim 20 wherein:

R$^1$ represents a methyl group or an ethyl group;

R$^2$ represents a hydrogen atom or a methyl group;

R$^3$ represents a hydrogen atom or an acetyl group which is optionally substituted with a substituent selected from the group consisting of halogen atoms, cyano groups, hydroxy groups, alkoxy groups having from 1 to 3 carbon atoms, alkylthio groups having from 1 to 3 carbon atoms, alkanoyloxy groups having from 1 to 4 carbon atoms, amino groups, amino groups substituted with 1 or 2 substituents selected from the group consisting of alkyl groups having from 1 to 3 carbon atoms atoms, alkanoyl groups having from 1 to 4 carbon atoms, alkylsulfonyl groups in which the alkyl moiety has from 1 to 3 carbons and alkoxycarbonyl groups in which the alkoxy moiety has from 1 to 4 carbon atoms, and saturated 4- to 6-membered heterocyclic ring groups containing one ring nitrogen atom and optionally containing one further ring heteroatom selected from the group consisting of sulfur atoms, oxygen atoms and nitrogen atoms, said heterocyclic ring groups optionally being substituted with an oxo group; and the moiety -a- together with the carbon atom to which it is attached form a cyclopentyl group.

22. A compound of formula (I) or an agriculturally, horticulturally, pharmaceutically or veterinarily acceptable salt thereof according to claim 15, wherein:

R$^1$ represents a methyl group or an ethyl group;

R$^2$ represents a hydrogen atom;

R$^3$ represents a hydrogen atom, an acetyl group, a hydroxyacetyl group, a methoxyacetyl group, an ethoxyacetyl group or a trifluoroacetyl group; and the moiety -a- together with the carbon atom to which it is attached form a cyclopentyl group.

23. A compound of formula (I) or an agriculturally, horticulturally, pharmaceutically or veterinarily acceptable salt thereof according to claim 1 wherein:

R$^1$ represents a methyl group or an ethyl group;

R$^2$ represents a hydrogen atom;

R$^3$ represents a methoxyacetyl group; and the moiety -a- together with the carbon atom to which it is attached form a cyclopentyl group.

24. A compound of formula (I) or a pharmaceutically acceptable salt thereof according to claim 1, wherein R$^1$ is methyl group, ethyl group, isopropyl group or s-butyl group;

R$^2$ is hydrogen atom or C$_1$–C$_3$ alkyl group;

R$^3$ is hydrogen atom, C$_1$–C$_4$ alkonoyl group which is optionally substituted with 1 or 2 substitutents independently selected from substituent group A, C$_1$–C$_3$ alkylsulfonyl group, C$_2$–C$_5$ alkoxycarbonyl group, or R$^2$ and R$^3$ are joined together with the nitrogen to which they are attached to form a saturated 4- to 6-membered cyclic amino group;

substituent group A is halogen atom, cyano group, hydroxy group, C$_1$–C$_3$ alkoxy group, C$_1$–C$_3$ alkylthio group, C$_1$–C$_4$ alkanoyloxy group, amino group or substituted amino group; and the moiety -a- together with the carbon atom to which it is attached form a cyclopentyl group;

with the proviso that both of R$^2$ and R$^3$ are not hydrogen atoms.

25. A compound of formula (I) according to claim 1 or a pharmaceutically salt thereof, wherein R$^1$ is a methyl or ethyl group, R$^2$ is hydrogen, R$^3$ is an acetyl group, hydroxyacetyl group, C$_2$–C$_3$ alkoxyacetyl group, or trifluoroacetyl group and the moiety -a- together with the carbon atom to which it is attached form a cyclopentyl group.

26. A compound of formula (I) according to claim 1 or an agriculturally, horticulturally, pharmaceutically or veterinarily acceptable salt thereof selected from the following group:

13-[1-(4-aminophenyl)cyclopentanecarbonyloxy]-5-hydroxymilbemycin A$_4$;

13-[1-(4-acetylaminophenyl)cyclopentanecarbonyloxy]-5-hydroxymilbemycin A$_4$

13-[1-(4-cyanoacetylaminophenyl)cyclopentanecarbonyloxy]-5-hydroxymilbemycin A$_4$;

13-[1-(4-hydroxyacetylaminophenyl)cyclopentanecarbonyloxy]-5-hydroxy-milbemycin A$_4$;

13-[1-(4-methoxyacetylaminophenyl)cyclopentanecarbonyloxy]-5-hydroxy-milbemycin A$_4$;

13-[1-(4-methanesulfonylaminophenyl)cyclopentanecarbonyloxy]-5-hydroxy-milbemycin A$_4$;

13-[1-(4-methoxyacetylaminophenyl)cyclopentanecarbonyloxy]-5-hydroxy-milbemycin A$_3$;

13-[1-(4-methanesulfonylaminophenyl)cyclopentanecarbonyloxy]-5-hydroxy-milbemycin A$_3$;

13-[1-(4-methoxyacetylaminophenyl)cyclobutanecarbonyloxy]-5-hydroxy-milbemycin A$_4$;

13-[1-(4-methanesulfonylaminophenyl)cyclobutanecarbonyloxy]-5-hydroxy-milbemycin A$_4$;

13-{1-[4-(N-acetyl-N-methylglycylamino)phenyl]cyclopentanecarbonyloxy}-5-hydroxymilbemycin A$_4$;

13-[1-(4-hydroxyacetylaminophenyl)cyclopentanecarbonyloxy]-5-hydroxy-milbemycin A$_3$, 13-[1-(4-hydroxyacetylaminophenyl)cyclobutanecarbonyloxy]-5-hydroxy-milbemycin A$_4$;

13-[1-(4-hydroxyacetylaminophenyl)cyclobutanecarbonyloxy]-5-hydroxy-milbemycin A$_3$;

13-[1-(4-methoxyacetylaminophenyl)cyclobutanecarbonyloxy]-5-hydroxy-milbemycin A$_3$, and 13-[1-(4-methanesulfonylaminophenyl)cyclobutanecarbonyloxy]-5-hydroxy-milbemycin A$_3$.

27. A compound of formula (I) according to claim 1 which is 13-[1-(4-methoxyacetylaminophenyl)cyclopentanecarbonyloxy]-5-hydroxymilbemycin A$_4$ or an agriculturally, horticulturally, pharmaceutically or veterinarily acceptable salt thereof.

28. A compound of formula (I) according to claim 27 which is said compound or a pharmaceutical salt thereof.

29. A compound of formula (I) according to claim 1 which is 13-[1-(4-methoxyacetylaminophenyl)cyclopentanecarbonyloxy]-5-hydroxymilbemycin A$_3$ or an agriculturally, horticulturally, pharmaceutically or veterinarily acceptable salt thereof.

30. A compund of formula (I) according to claim 29 which is said compound or a pharmaceutical salt thereof.

31. An anthelmintic, acaricidal or insecticidal composition comprising an effective amount of an anthelmintic, acaricidal or insecticidal compound in admixture with an agriculturally, horticulturally, pharmaceutically or veterinarily acceptable carrier, wherein said compound is selected from the group consisting of compounds of formula (I) and agriculturally, horticulturally, pharmaceutically or veterinarily acceptable salts thereof according to any one of claims 1 to 30.

32. A composition according to claim 31 suitable for use in veterinary applications against acarids, helminths or insects which are parasitic on mammals.

33. A composition according to claim 31 suitable for use as an insecticide against cat fleas (*Ctenocephalides felis*) or dog fleas (*Ctenocephalides canis*).

34. A method of treating plants or animals or sites infested by organisms selected from the group consisting of acarids, helminths and insects or to protect such plants or animals or sites from damage by said organisms which comprises applying an effctive amount of an active compound to said plants or animals or to parts of or reproductive matter of said plants of to a site including said plants, said animals or parts of said plants or reproductive matter of said plants, or other sites, wherein the active compound is selected from the group consisting of compounds of formula (I) and agriculturally, horticulturally, pharmaceutically or veterinarily acceptable salts thereof according to any one of claim 1 to 30.

35. A method according to claim 34 for treating or protecting mammals from said acarids, helminths or insects which are parasitics on said mammals.

36. A method according to claim 35 wherein said mammals is a human.

37. A method according to claim 35 for treating animals from cat fleas (*Ctenocephalides felis*) or dog fleas (*Ctenocephalides canis*).

38. A method according to claim 37 wherein said mammals is a human.

* * * * *